United States Patent
Werneth et al.

(10) Patent No.: US 10,004,459 B2
(45) Date of Patent: Jun. 26, 2018

(54) CATHETER SYSTEM AND METHODS OF MEDICAL USES OF SAME, INCLUDING DIAGNOSTIC AND TREATMENT USES FOR THE HEART

(71) Applicant: ACUTUS MEDICAL, INC., San Diego, CA (US)

(72) Inventors: Randell L. Werneth, Boise, ID (US); Graydon E. Beatty, Bloomington, MN (US); Timothy J. Corvi, Carlsbad, CA (US); J. Christopher Flaherty, Auburndale, FL (US); Marcus Frederick Julian, Vista, CA (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 0 days. days.

(21) Appl. No.: 14/422,941

(22) PCT Filed: Aug. 30, 2013

(86) PCT No.: PCT/US2013/057579
§ 371 (c)(1),
(2) Date: Feb. 20, 2015

(87) PCT Pub. No.: WO2014/036439
PCT Pub. Date: Mar. 6, 2014

(65) Prior Publication Data
US 2015/0223757 A1    Aug. 13, 2015

Related U.S. Application Data

(60) Provisional application No. 61/695,535, filed on Aug. 31, 2012.

(51) Int. Cl.
*A61B 5/00* (2006.01)
*A61B 8/00* (2006.01)
(Continued)

(52) U.S. Cl.
CPC .......... *A61B 5/6858* (2013.01); *A61B 5/0205* (2013.01); *A61B 5/042* (2013.01);
(Continued)

(58) Field of Classification Search
CPC .... A61B 5/6852; A61B 5/6858; A61B 8/4494
See application file for complete search history.

(56) References Cited

U.S. PATENT DOCUMENTS

| 5,041,973 A | 8/1991 | Lebron et al. |
| 5,156,151 A | 10/1992 | Imran |

(Continued)

FOREIGN PATENT DOCUMENTS

| CA | 2829626 | 9/2012 |
| CN | 201223445 | 4/2009 |

(Continued)

OTHER PUBLICATIONS

ISRWO dated May 20, 2014 in International application No. PCT/US14/15261.
(Continued)

*Primary Examiner* — William Levicky
(74) *Attorney, Agent, or Firm* — Onello & Mello, LLP

(57) ABSTRACT

The present invention includes systems, devices and methods for treating and/or diagnosing a heart arrhythmia, such as atrial fibrillation. Specifically, the present invention provides a system including a diagnostic catheter and an ablation catheter. The diagnostic catheter includes a shaft, multiple dipole mapping electrodes and multiple ultrasound transducers. The ablation catheter is slidingly received by the diagnostic catheter shaft.

34 Claims, 11 Drawing Sheets

(51) Int. Cl.

| | |
|---|---|
| *A61B 8/12* | (2006.01) |
| *A61B 5/042* | (2006.01) |
| *A61B 18/14* | (2006.01) |
| *A61B 5/0205* | (2006.01) |
| *A61B 5/046* | (2006.01) |
| *A61B 5/0464* | (2006.01) |
| *A61B 5/06* | (2006.01) |
| *A61B 17/22* | (2006.01) |
| *A61B 18/02* | (2006.01) |
| *A61B 18/18* | (2006.01) |
| *A61B 18/20* | (2006.01) |
| *A61B 17/00* | (2006.01) |
| *A61B 18/00* | (2006.01) |
| *A61N 1/05* | (2006.01) |
| *A61B 5/053* | (2006.01) |
| *A61B 34/30* | (2016.01) |

(52) U.S. Cl.
CPC .......... *A61B 5/0422* (2013.01); *A61B 5/4836* (2013.01); *A61B 5/6852* (2013.01); *A61B 8/12* (2013.01); *A61B 8/445* (2013.01); *A61B 8/4494* (2013.01); *A61B 18/1492* (2013.01); *A61B 5/046* (2013.01); *A61B 5/0464* (2013.01); *A61B 5/0538* (2013.01); *A61B 5/065* (2013.01); *A61B 5/6859* (2013.01); *A61B 17/22012* (2013.01); *A61B 18/02* (2013.01); *A61B 18/1815* (2013.01); *A61B 18/20* (2013.01); *A61B 2017/00318* (2013.01); *A61B 2018/0016* (2013.01); *A61B 2018/00267* (2013.01); *A61B 2018/00351* (2013.01); *A61B 2018/00577* (2013.01); *A61B 2018/00648* (2013.01); *A61B 2018/00839* (2013.01); *A61B 2018/00982* (2013.01); *A61B 2018/1465* (2013.01); *A61B 2018/1467* (2013.01); *A61B 2018/1475* (2013.01); *A61B 2034/301* (2016.02); *A61B 2562/06* (2013.01); *A61N 1/056* (2013.01)

(56) References Cited

U.S. PATENT DOCUMENTS

| | | | |
|---|---|---|---|
| 5,482,472 A | 1/1996 | Garoni et al. | |
| 5,499,981 A | 3/1996 | Kordis | |
| 5,555,883 A | 9/1996 | Avitall | |
| 5,595,183 A | 1/1997 | Swanson et al. | |
| 5,601,084 A | 2/1997 | Sheehan et al. | |
| 5,662,108 A | 9/1997 | Budd et al. | |
| 5,722,402 A * | 3/1998 | Swanson | A61B 5/0422 600/374 |
| 5,722,416 A | 3/1998 | Swanson et al. | |
| 5,740,808 A | 4/1998 | Panescu et al. | |
| 5,759,158 A * | 6/1998 | Swanson | A61B 5/0422 600/508 |
| 5,795,298 A | 8/1998 | Vesely | |
| 5,795,299 A | 8/1998 | Eaton et al. | |
| 5,820,568 A | 10/1998 | Willis | |
| 5,876,336 A | 3/1999 | Swanson et al. | |
| 5,928,228 A | 7/1999 | Kordis et al. | |
| 5,968,040 A | 10/1999 | Swanson et al. | |
| 6,014,590 A | 1/2000 | Whayne et al. | |
| 6,024,703 A * | 2/2000 | Zanelli | A61B 18/20 600/437 |
| 6,066,096 A | 5/2000 | Smith et al. | |
| 6,086,532 A | 7/2000 | Panescu et al. | |
| 6,107,699 A | 8/2000 | Swanson | |
| 6,187,032 B1 | 2/2001 | Ohyu et al. | |
| 6,188,928 B1 | 2/2001 | Noren et al. | |
| 6,216,027 B1 | 4/2001 | Willis et al. | |
| 6,216,043 B1 | 4/2001 | Swanson et al. | |
| 6,240,307 B1 * | 5/2001 | Beatty | A61B 5/04085 600/374 |
| 6,301,496 B1 | 10/2001 | Reisfeld | |
| 6,400,981 B1 | 6/2002 | Govari | |
| 6,490,474 B1 | 12/2002 | Willis et al. | |
| 6,574,492 B1 | 6/2003 | Ben-Haim et al. | |
| 6,640,119 B1 | 10/2003 | Budd et al. | |
| 6,716,166 B2 * | 4/2004 | Govari | A61B 5/0422 600/437 |
| 6,728,562 B1 | 4/2004 | Budd et al. | |
| 6,772,004 B2 | 8/2004 | Rudy | |
| 6,773,402 B2 | 8/2004 | Govari et al. | |
| 6,824,515 B2 | 11/2004 | Suorsa et al. | |
| 6,826,420 B1 | 11/2004 | Beatty et al. | |
| 6,826,421 B1 | 11/2004 | Beatty et al. | |
| 6,895,267 B2 | 5/2005 | Panescu et al. | |
| 6,939,309 B1 | 9/2005 | Beatty et al. | |
| 6,950,689 B1 | 9/2005 | Willis et al. | |
| 6,970,733 B2 | 11/2005 | Willis et al. | |
| 6,978,168 B2 | 12/2005 | Beatty et al. | |
| 6,990,370 B1 | 1/2006 | Beatty et al. | |
| 7,187,964 B2 | 3/2007 | Khoury | |
| 7,285,119 B2 | 10/2007 | Stewart et al. | |
| 7,289,843 B2 | 10/2007 | Beatty et al. | |
| 7,291,146 B2 | 11/2007 | Steinke et al. | |
| 7,505,810 B2 | 3/2009 | Harley et al. | |
| 7,573,182 B2 | 8/2009 | Savage | |
| 7,766,838 B2 | 8/2010 | Yagi et al. | |
| 7,841,986 B2 | 11/2010 | He et al. | |
| 7,918,793 B2 | 4/2011 | Altmann et al. | |
| 7,953,475 B2 | 5/2011 | Harley et al. | |
| 8,103,327 B2 | 1/2012 | Harlev et al. | |
| 8,147,486 B2 | 4/2012 | Honour et al. | |
| 8,150,499 B2 | 4/2012 | Gelbart et al. | |
| 8,175,680 B2 | 5/2012 | Panescu | |
| 8,208,998 B2 | 6/2012 | Beatty et al. | |
| 8,346,339 B2 | 1/2013 | Kordis et al. | |
| 8,360,786 B2 | 1/2013 | Duryea | |
| 8,364,234 B2 | 1/2013 | Kordis et al. | |
| 8,412,307 B2 | 4/2013 | Willis et al. | |
| 8,417,313 B2 | 4/2013 | Scharf et al. | |
| 8,428,690 B2 | 4/2013 | Li et al. | |
| 8,447,377 B2 | 5/2013 | Harlev et al. | |
| 8,454,596 B2 | 6/2013 | Ma et al. | |
| 8,465,433 B2 | 6/2013 | Zwirn | |
| 8,512,255 B2 | 8/2013 | Scharf et al. | |
| 8,700,119 B2 | 4/2014 | Scharf et al. | |
| 8,755,861 B2 | 6/2014 | Harlev et al. | |
| 8,825,130 B2 | 9/2014 | Just et al. | |
| 8,825,134 B2 | 9/2014 | Danehorn | |
| 8,918,158 B2 | 12/2014 | Scharf et al. | |
| 8,934,988 B2 | 1/2015 | Persson et al. | |
| 8,948,837 B2 | 2/2015 | Harlev et al. | |
| 8,968,299 B2 | 3/2015 | Kauphusman et al. | |
| 8,979,839 B2 | 3/2015 | De La Rama et al. | |
| 8,989,842 B2 | 3/2015 | Li et al. | |
| 9,011,423 B2 | 4/2015 | Brewster et al. | |
| 9,037,259 B2 | 5/2015 | Mathur | |
| 9,044,245 B2 | 6/2015 | Condie et al. | |
| 9,167,982 B2 | 10/2015 | Scharf et al. | |
| 9,186,081 B2 | 11/2015 | Afonso et al. | |
| 9,186,212 B2 | 11/2015 | Nabutovsky et al. | |
| 9,192,318 B2 | 11/2015 | Scharf et al. | |
| 9,351,789 B2 | 5/2016 | Novichenok et al. | |
| D758,596 S | 6/2016 | Perryman et al. | |
| 9,474,486 B2 | 10/2016 | Eliason et al. | |
| 9,480,525 B2 | 11/2016 | Lopes et al. | |
| 9,486,355 B2 | 11/2016 | Gustus et al. | |
| 9,492,227 B2 | 11/2016 | Lopes et al. | |
| 9,492,228 B2 | 11/2016 | Lopes et al. | |
| 9,504,395 B2 | 11/2016 | Scharf et al. | |
| 9,526,573 B2 | 12/2016 | Lopes et al. | |
| 9,549,708 B2 | 1/2017 | Mercanzini et al. | |
| 9,579,149 B2 | 2/2017 | Kelly et al. | |
| 9,585,588 B2 | 3/2017 | Marecki et al. | |
| 9,610,024 B2 | 4/2017 | Scharf et al. | |
| 9,675,401 B2 | 6/2017 | Lopes et al. | |
| 9,713,730 B2 | 7/2017 | Mathur et al. | |
| 9,717,555 B2 | 8/2017 | Chan et al. | |

(56) References Cited

U.S. PATENT DOCUMENTS

| | | |
|---|---|---|
| 9,717,559 B2 | 8/2017 | Ditter et al. |
| 9,757,044 B2 | 9/2017 | Scharf et al. |
| 9,827,039 B2 | 11/2017 | Dandler et al. |
| 2001/0007070 A1 | 7/2001 | Stewart et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0153907 A1 | 8/2003 | Suorsa et al. |
| 2003/0158477 A1 | 8/2003 | Panescu |
| 2003/0231789 A1 | 12/2003 | Willis et al. |
| 2003/0236466 A1 | 12/2003 | Tarjan et al. |
| 2004/0254437 A1 | 12/2004 | Hauck et al. |
| 2005/0059880 A1 | 3/2005 | Mathias et al. |
| 2005/0113665 A1 | 5/2005 | Mohr et al. |
| 2005/0148836 A1* | 7/2005 | Kleen ............... A61B 5/0066 600/374 |
| 2005/0203375 A1 | 9/2005 | Willis et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0219551 A1 | 9/2007 | Honour et al. |
| 2007/0232949 A1 | 10/2007 | Saksena |
| 2008/0009758 A1 | 1/2008 | Voth |
| 2008/0287777 A1 | 11/2008 | Li et al. |
| 2009/0024086 A1 | 1/2009 | Zhang et al. |
| 2009/0076483 A1* | 3/2009 | Danehorn ............. A61M 25/01 604/528 |
| 2009/0131930 A1 | 5/2009 | Gelbart et al. |
| 2009/0143651 A1 | 6/2009 | Kallback et al. |
| 2009/0171274 A1 | 7/2009 | Harlev et al. |
| 2009/0264781 A1 | 10/2009 | Scharf |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0298690 A1 | 11/2010 | Scharf |
| 2011/0077526 A1 | 3/2011 | Zwirn |
| 2011/0118726 A1 | 5/2011 | De La Rama et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0271138 A1 | 10/2012 | Kordis et al. |
| 2012/0271139 A1 | 10/2012 | Kordis et al. |
| 2012/0277574 A1 | 11/2012 | Panescu |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0178851 A1 | 7/2013 | Lopes et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0245621 A1 | 9/2013 | Persson et al. |
| 2013/0253298 A1 | 9/2013 | Harlev et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0121470 A1 | 5/2014 | Scharf et al. |
| 2014/0180150 A1 | 6/2014 | Scharf et al. |
| 2014/0257069 A1 | 9/2014 | Eliason et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0208938 A1 | 7/2015 | Houben et al. |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2017/0035486 A1 | 2/2017 | Lopes et al. |

FOREIGN PATENT DOCUMENTS

| | | |
|---|---|---|
| CN | 201275144 | 7/2009 |
| EP | 1166714 | 1/2002 |
| EP | 1760661 | 3/2007 |
| EP | 1779787 | 5/2007 |
| EP | 2051625 | 2/2008 |
| EP | 2252203 | 11/2010 |
| EP | 2683293 | 1/2014 |
| JP | 08501477 | 2/1996 |
| JP | 10137207 | 5/1998 |
| JP | 2001070269 | 3/2001 |
| JP | 2002113004 | 4/2002 |
| JP | 2002522106 | 7/2002 |
| JP | 2003511098 | 3/2003 |
| JP | 2004350702 | 12/2004 |
| JP | 2006511296 | 4/2006 |
| JP | 2011507656 | 3/2011 |
| WO | 9406349 | 3/1994 |
| WO | 9905971 | 2/1999 |
| WO | 09905971 | 2/1999 |
| WO | 0007501 | 2/2000 |
| WO | 0245608 | 6/2002 |
| WO | 2002045608 | 6/2002 |
| WO | 2003026722 | 4/2003 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012092016 | 7/2012 |
| WO | 2012100184 | 7/2012 |
| WO | 2012100185 | 7/2012 |
| WO | 2012122517 | 9/2012 |
| WO | 2014036439 | 3/2014 |
| WO | 2014130169 | 8/2014 |
| WO | 2015148470 | 10/2015 |

OTHER PUBLICATIONS

PCT ISRWO dated Jun. 5, 2014, issued in corresponding PCT Application No. PCT/US2013/057579.

Gupta, et al., "Point of View Cardiac Mapping: Utility or Futility?", Indian Pacing and Electro hysiology Journal, vol. 2, No. 1, Jan. 1, 2002, pp. 20-32.

European SR dated Sep. 29, 2014, issued in European Application No. 13176658.6.

International Search Report dated Mar. 10, 2015 issued in corresponding International Application No. PCT/US14/54942.

International Search Report and Written Opinion dated Jun. 26, 2015 issued in International Application No. PCT/US2015/022187.

"Transducer-Electrode Arrangement" Specification, Drawings, Claims and Prosecution History, of U.S. Appl. No. 29/475,273, filed

(56) References Cited

OTHER PUBLICATIONS

Dec. 2, 2013, by Randell L. Wemeth, et al, which is stored in the United States Patent and Trademark Office (USPTO).
International Search Report and Written Opinion dated Mar. 5, 2013, issued in related International Application No. PCT/US2012/028593.
Scharf, et al., Delcaration under 37 C.F.R. 1.132, Nov. 15, 2012.
Pullan, et al., "The Inverse Problem of Electrocardiography," Northeastern University Electrical and Computer Engineering, Feb. 23, 2007.
He, et al., "An Equivalent Body Surface Charge Model Representing Three-Dimensional Bioelectrical Activity," IEEE Transactions on Biomedical Engineering, 42.7 (1995), pp. 637-646.
International Search Report issued in related International Application No. PCT/CH2007/000380.
International Search Report dated Oct. 7, 2009 issued in corresponding International Application No. PCT/IB2009/000071.
Partial European Search Report dated Apr. 29, 2014, issued in corresponding European Application No. 13176658.
Della Bella, et al., "Non-contact mapping to guide catheter ablation of untolerated ventricular tachycardia" European Heart Journal; 23(9): 742-754 (2002).
International Search Report dated Sep. 10, 2014 issued in corresponding International Application No. PCT/US14/54942.
International Search Report dated Jun. 5, 2014 issued in corresponding PCT application WO 2014/036439.
William G. Stevenson et al: "Recording Techniques for Clinical Electrophysiology" Journal of Cardiovascular Electrophysiology. vol. 16 No. 91, Sep. 2005, pp. 1017-1022.
Wolfgang Nolting: Elektrodynamik—Grundkurs Theoretische Physik 3 Springer Spektrum pp. D 89- D 91.
Office Action dated Mar. 9, 2016 in corresponding European Patent Application No. 09702094.5.
European Office Action dated Feb. 29, 2016 issued in corresponding European Application No. 07 785 075.8-1657.
Van Oosterom A: "Solidifying the solid angle." 2002 Journal of Electrocardiology 2002 vol. 35 Suppl pp. 181-192 ISSN: 0022-0736.
Office Action dated Mar. 9, 2016 in corresponding European Patent Application No. 13176658.6.
Examiner's Report dated Dec. 22, 2015 in related Canadian Application No. 2656898.
Office Action dated Apr. 27, 2016 in corresponding Canadian Application No. 2747859.
Extended European Search Report dated Jul. 8, 2016 in related European Application No. 14748567.6.
Patent Examination Report No. 3 dated Sep. 21, 2016 in related Australian Application No. 2012225250.
Office Action dated May 30, 2016 in related Australian Patent Application No. 2012225250.
Chinese Office Action dated Apr. 17, 2017 issued in corresponding Chinese Application No. 201480018328.4.
Canadian Office Action dated Apr. 26, 2017 issued in corresponding Canadian Application No. 2932956.
European Office Action dated Mar. 21, 2017 issued in corresponding European Application No. 07785075.8.
Jackson, JD, "Surface Distributions of Charges and Dipoles and Discontinuities in the Electric Field and Potential", Classical Electrodynamics, 3rd edition, Dec. 1998, pp. 31-34.
Japanese Office Action dated Jan. 31, 2017 issued in corresponding Japanese Application No. 2013-557926, with English language summary.
Office Action dated Mar. 30, 2017 in corresponding Canadian Application No. 2747859.
Leif et al., "Geometric modeling based on polygonal meshes", Eurographics 2000 Tutorial, Aug. 21, 2000.
Extended European Search Report dated Oct. 18, 2017, issued in European Application No. 15768711.
Office Action dated Oct. 10, 2017, issued in Application No. 2015-557091 with machine translation to English.
Office Action dated Nov. 7, 2017, issued in European Application No. 15768711.
Japanese Office Action dated Sep. 26, 2017 issued in corresponding Japanese Application No. 2017-155346, with English translation.
Canadian Office Action dated Nov. 27, 2017 issued in corresponding Canadian Application No. 2829626.
Australian Office Action dated Jul. 6, 2017, issued in Australian Application No. 2014/214756.
Australian Office Action dated Jun. 27, 2017 issued in Australian Application No. 2013308531.
Japanese Notice of Allowance dated Jul. 11, 2017 issued in Japanese Application No. 2013-557926.
Japanese Office Action dated Jun. 27, 2017 issued in corresponding Japanese Application No. 2015-530101, with English language translation.
ISRWO dated Aug. 11, 2016 issued in corresponding International Application No. PCT/US2016/032017.
ISRWO dated Aug. 8, 2016 issued in corresponding European Application No. PCT/US2016/031823.
ISRWO dated Aug. 18, 2016 issued in corresponding International Application No. PCT/US16/32420.
ISRWO dated Dec. 12, 2017 issued in corresponding International Application No. PCT/US2017/056064.
ISRWO dated Sep. 25, 2017, issued in Application No. PCT/US17/30922.
ISRWO dated Aug. 4, 2017, issued in Application No. PCT/US17/30915.
Canadian Office Action dated Jan. 22, 2018 issued in corresponding Canadian Application No. 2932956.
Australian Office Action dated Feb. 26, 2018 issued in Australian Application No. 2017201560.
Decision dated Jan. 16, 2018 issued for European Patent Application No. 09702094.5.
Decision dated Jan. 18 issued for European Patent Application No. 13176658.6.
European Office Action dated Jan. 31, 2018, issued in corresponding European Application No. 13763151.1.
Australian Office Action dated Mar. 17, 2018 issued in Australian Application No. 2013308531.
Notice of Acceptance dated Apr. 19, 2018 issued in corresponding Australian Application No. 2013308531.

\* cited by examiner

CATHETER SYSTEM AND METHODS OF MEDICAL USES OF SAME, INCLUDING DIAGNOSTIC AND TREATMENT USES FOR THE HEART

RELATED APPLICATIONS

The present application claims priority under 35 USC 119(e) to U.S. Provisional Patent Application No. 61/695,535, entitled SYSTEM AND METHOD FOR DIAGNOSING AND TREATING HEART TISSUE, filed Aug. 31, 2012, the contents of which are incorporated herein by reference in their entirety.

The present application, while not claiming priority to, may be related to U.S. patent application Ser. No. 13/858,715, entitled Method and Device for Determining and Presenting Surface Charge and Dipole Densities on Cardiac Walls, filed Apr. 8, 2013, which is a continuation of U.S. patent application Ser. No. 12/376,270, entitled Method and Device for Determining and Presenting Surface Charge and Dipole Densities on Cardiac Walls, filed Feb. 3, 2009, published as US2009264781, which was a 35 USC 371 national stage filing of PCT Application No. CH2007/000380, entitled Method and Device for Determining and Presenting Surface Charge and Dipole Densities on Cardiac Walls, filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 13/946,712, entitled A Device and Method for the Geometric Determination of Electrical Dipole Densities on the Cardiac Wall, filed Jul. 19, 2013, which is a continuation of U.S. patent application Ser. No. 12/863,411, entitled A Device and Method for the Geometric Determination of Electrical Dipole Densities on the Cardiac Wall, filed Jul. 16, 2010, published as US20100298690, which was a 35 USC 371 a national stage application of Patent Cooperation Treaty Application No. PCT/IB09/00071 filed Jan. 16, 2009, entitled A Device and Method for the Geometric Determination of Electrical Dipole Densities on the Cardiac Wall, published as WO 2009/090547, which claimed priority to Swiss Patent Application 00068/08 filed Jan. 17, 2008, each of which is hereby incorporated by reference.

The present application, while not claiming priority to, may be related to Applicant's co-pending international application, Serial Number PCT/US2012/028593, entitled Device and Method for the Geometric Determination of Electrical Dipole Densities on the Cardiac Wall, the entirety of which is incorporated herein.

FIELD OF INVENTION

The invention relates to the field of medical devices used in electrophysiology, and more particularly to the field of devices for mapping activity of internal organs, catheters for treating same, and methods for using such devices and catheters.

BACKGROUND

The use of electrodes within a body for measuring certain electrical characteristics of the heart is routinely performed, sometimes referred to as cardiac mapping. And the use of ablation catheters to selectively ablate nerves or tissue, for example, within the body is also routinely performed. Cardiac mapping and ablation are performed separately, using different, specialized devices or systems.

An ablation catheter can be used, for example, in a medical procedure to treat some types of arrhythmias, which are problems with the rate or rhythm of the heartbeat. An ablation catheter is a long, thin, flexible tube that is put into a blood vessel in the arm, groin (upper thigh), or neck of the patient and guided into the heart through the blood vessel. In catheter ablation, radiofrequency (RF) energy is usually used to produce heat from radiofrequency energy that selectively destroys the heart tissue.

For cardiac mapping, as an example, currently electrodes can be localized within the body either by a permanent magnetic field, a magnetic field generated by electromagnets, or an impedance measurement.

The Carto 3 System by Biosense Webster, Inc. is an example of an electromagnetic field measurement system, in accordance with the prior art. Such a system needs specialized electrodes with electromagnetic coils.

The Localisa® Intracardiac Navigation System by Medtronic, Inc. is an example of an impedance measurement system, in accordance with the prior art. (Localisa is registered as a United States trademark by Medtronic Inc.) Such a system can be inaccurate due to tissue anisotropy and respiration.

SUMMARY

Provided is an ablation system comprising a diagnostic catheter and an ablation catheter. The diagnostic catheter is configured to provide dipole mapping information as well as to slidingly receive the ablation catheter. The system is configured to provide anatomical mapping information, as well as to identify the location of ("localize") electrodes within and/or upon the human body by delivering and recording electric signals between them. In accordance with various aspects of the present invention, a single conduit can provide left atrial access and maneuvering within the atrium to map and/or ablate cardiac tissue, avoiding the need to perform a double transseptal puncture. Localization of electrodes enables visualization and precise maneuvering of one or more catheters of the system. Navigation of the one or more catheters can be performed based on the localization information.

In accordance with one aspect of the present disclosure, an ablation system comprises an ablation catheter and a diagnostic catheter. The ablation catheter comprises an elongate shaft with a distal portion and at least one ablation element positioned on the ablation catheter shaft distal portion and configured to delivery energy to tissue. The diagnostic catheter comprises an elongate shaft comprising a distal end where the diagnostic catheter shaft is configured to slidingly receive the distal portion of the ablation catheter shaft; an expandable assembly mounted to the diagnostic catheter shaft and configured to transition from a compacted state to an expanded state; a plurality of dipole mapping electrodes coupled to the expandable assembly; and a plurality of ultrasound transducers coupled to the expandable assembly. The ablation catheter may be used to treat a patient, for example, heart tissue of a patient.

The system can be configured to treat at least one of an atrial fibrillation patient or a ventricular tachycardia patient.

The system can be configured to treat at least one of the left atrium of the patient or the left ventricle of the patient, while utilizing a single transseptal puncture.

The system can be configured to treat the left ventricle of the patient, while utilizing a single crossing of the aortic valve to access the left ventricle.

The diagnostic catheter can be configured to provide information selected from the group consisting of: surface unipolar voltage information; surface bipolar voltage information; surface charge density information; monophasic action potential information; anatomical geometry information such as heart wall position and heart wall thickness information; and combinations of these. In some embodiments, the system further comprises a memory storage module comprising criteria information, and the information provided by the diagnostic catheter can be compared to the stored criteria information.

The diagnostic catheter can be configured to be positioned in at least one of the left atrium or the left ventricle.

The diagnostic catheter can comprise a distal portion and a steering assembly, and the steering assembly can be configured to steer the diagnostic catheter distal portion in one or more directions. In some embodiments, the steering assembly comprises a robotic steering assembly.

The diagnostic catheter can comprise a distal portion with a diameter less than or equal to 15 Fr.

The diagnostic catheter shaft can be configured to slidingly receive the distal portion of the ablation catheter and the distal portion of an additional elongate device. The additional elongate device can comprise a catheter selected from the group consisting of: a diagnostic catheter such as a diagnostic catheter constructed and arranged to record signals from the left atrium, the left ventricle, the right atrium, the Bundle of HIS, the right ventricular apex, a pulmonary vein or the coronary sinus; a catheter with a linear array of electrodes; a catheter with a helical array of electrodes; a pacing catheter; an energy delivery catheter such as a catheter constructed and arranged to deliver radiofrequency energy, cryogenic energy, laser energy or ultrasound energy; and combinations of these.

The expandable assembly can be positioned on the distal end of the diagnostic catheter shaft.

The expandable assembly can be configured to radially expand. In some embodiments, the system further comprises a sheath with a distal end, and the expandable assembly can be configured to radially expand as it exits the sheath distal end.

The expandable assembly can comprise a plurality of expandable members. The plurality of expandable members can be formed of a material comprising a shape memory alloy, for example a shape memory alloy comprising Nitinol. The plurality of expandable members can be formed of a material comprising a shape memory polymer, for example a shape memory polymer comprising a triple shape acrylic.

The expandable assembly can comprise a plurality of bendable splines, where each spline comprises a proximal end and a distal end. Each spline can further comprise a set of spaced dipole mapping electrodes. The set of spaced dipole mapping electrodes can comprise at least 4 dipole mapping electrodes, or at least 6 dipole mapping electrodes, or at least 8 dipole mapping electrodes. Each spline can further comprise a set of spaced ultrasound transducers. The set of spaced ultrasound transducers can comprise at least 4 ultrasound transducers, or at least 6 ultrasound transducers, or at least 8 ultrasound transducers. Each spline can further comprise at least two of the plurality of dipole mapping electrodes and at least two of the plurality of ultrasound transducers. For example, one or more of the plurality dipole mapping electrodes can be disposed between two adjacent ultrasound transducers on each spline.

Each spline proximal end can be fixedly attached at a location proximate the diagnostic catheter elongate shaft distal end, and each spline distal end can be connected in a circumferential arrangement. The circumferential arrangement can define an opening when the expandable assembly is in an expanded state. The diagnostic catheter shaft can comprise a distal portion defining a central axis, and the opening can be relatively centered about the axis. The ablation catheter can comprise a distal end, and the opening can be positioned such that advancement of the ablation catheter through the diagnostic catheter causes the ablation catheter shaft distal end to tend to pass through the opening. The expandable assembly can further comprise two or more guide elements, for example two or more guide elements that can be configured such that during advancement of the ablation catheter through the diagnostic catheter, the ablation catheter distal end is directed by the guide elements to pass through the opening. The two or more guide elements can be configured to partially advance from the diagnostic catheter distal end as the diagnostic catheter transitions from its compacted state to its expanded state. The expandable assembly can further comprise a guide tube connected to the opening, for example the guide tube can be configured to partially advance from the diagnostic catheter distal end as the diagnostic catheter transitions from its compacted state to its expanded state.

The ablation catheter can comprise a distal end, and each spline can further comprise a mid portion positioned between its proximal end and its distal end, and the ablation catheter distal end can be configured to be radially deflected to cause the ablation catheter distal end to pass between a first spline mid portion and a second spline mid portion when the bendable splines are in an expanded state. The expandable assembly can further comprise two or more guide elements, for example where the deflection of the ablation catheter distal end further can cause the ablation catheter distal end to pass between two guide elements.

The plurality of dipole mapping electrodes can comprise non-polarizing metals. The plurality of dipole mapping electrodes can comprise non-noble metals constructed and arranged to oxidize when in contact with at least one of blood, blood plasma, or saline solutions. The plurality of dipole mapping electrodes can comprise a coating selected from the group consisting of: a metal oxide coating; a conductive polymer coating; and combinations of these. The plurality of dipole mapping electrodes can comprise a coating constructed to be at least one of electrochemically catalytic or directly reactive with at least one of blood, blood plasma or saline solutions. The plurality of dipole mapping electrodes can further comprise an outer layer, an inner layer positioned within the outer layer, where the outer layer can comprise an impedance lowering layer and the inner layer can be configured to bond to the outer layer. The plurality of dipole mapping electrodes can comprise a polarizing metal. The plurality of dipole mapping electrodes can comprise a noble metal.

The plurality of dipole mapping electrodes can comprise a quantity equal to the quantity of the plurality of ultrasound transducers. A number of dipole mapping electrodes can be greater than a number of ultrasound transducers. Each of the plurality of dipole mapping electrodes can be disposed between two ultrasound transducers. Each of the plurality of ultrasound transducers can be disposed between two dipole mapping electrodes.

The plurality of dipole mapping electrodes can comprise at least one dipole mapping electrode with an impedance of less than 10,000 ohms for frequencies above 0.1 hertz.

The plurality of ultrasound transducer can comprise an assembly selected from the group consisting of: single or multi-element piezoelectric ceramics; piezoelectric micromachined ultrasound transducers (pMUT); capacitive micro-machined ultrasound transducers (cMUT); piezoelectric polymers; and combinations of these.

The diagnostic catheter shaft can comprise a braided layer. The braided layer can comprise two or more electrical conductors positioned therein. The two or more electrical conductors can comprise two or more coaxial cables. At least one conductor can be electrically connected to a dipole mapping electrode, and at least one conductor can be electrically connected to an ultrasound transducer. At least one conductor can be positioned in the braided layer in a helical pattern.

The ablation catheter can comprise a distal end, and the at least one ablation element can be positioned on the ablation catheter distal end. The at least one ablation element can comprise multiple electrodes positioned in a linear array on the ablation catheter shaft distal portion. The ablation catheter can comprise multiple electrodes configured to deliver energy and record electrical signals. The ablation catheter can comprise multiple electrodes configured to deliver energy and record dipole mapping information.

The ablation catheter can comprise a steering mechanism configured to selectively maneuver the distal portion of the ablation catheter. The steering mechanism can comprise an anchoring element and one or more attached pull wires configured to enable uni-directional to multi-directional displacement of the ablation catheter distal portion. The steering mechanism can comprise a robotic steering mechanism.

The at least one ablation element can comprise at least one electrode. The at least one ablation element can comprise an ablation element selected from the group consisting of: electrode; vessel configured to deliver cryogenic energy; laser diode; optical fiber configured to deliver ablative energy; microwave energy delivery element; ultrasound energy delivery element; drug or other agent delivery element; and combinations of these. The at least one ablation element can be configured to deliver an energy form selected from the group consisting of: radiofrequency energy; cryogenic energy; laser energy; light energy; microwave energy; ultrasound energy; chemical energy; and combinations of these.

The system can further comprise a distance measurement assembly. The distance measurement assembly can produce a set of data representing the distance between each ultrasound transducer of the plurality of ultrasound transducers and a tissue surface orthogonal to each ultrasound transducer. The distance measurement assembly can be configured to deliver a signal to the diagnostic catheter plurality of ultrasound transducers, record a first generated signal from the diagnostic catheter plurality of ultrasound transducers, and produce a first set of distance information based on the recording of the first generated signal. The ablation catheter can comprise at least one ultrasound transducer, and the distance measurement assembly can be configured to deliver a signal to the ablation catheter at least one ultrasound transducer, record a second generated signal from the ablation catheter at least one ultrasound transducer, and produce a second set of distance information based on the recording of the second generated signal. In some embodiments, the system further comprises an accessory device comprising at least one ultrasound transducer, and the distance measurement assembly can be configured to deliver a signal to the accessory device at least one ultrasound transducer, record a second generated signal from the accessory device at least one ultrasound transducer, and produce a second set of distance information based on the recording of the second generated signal. The accessory device can comprise a device selected from the group consisting of: external ultrasound device; transesophageal echocardiography device; intracardiac echocardiography device; a catheter with a linear array of recording electrodes; a catheter with a helical array of recording electrodes; coronary sinus diagnostic catheter recording device; and combinations of these.

The system can comprise at least a first electrode and a second electrode and, the distance measurement assembly can produce data representing the distance between the first electrode and the second electrode. The first electrode can be configured to deliver an electrical signal, and the second electrode is configured to record the electrical signal delivered by the first electrode, and the distance measurement assembly can produce the data based on the recorded electrical signal. The delivered signal can comprise an electric current. The recorded signal can comprise a voltage. The distance measurement assembly can be configured to produce the first set of distance information based on a comparison of the first generated signal to the delivered signal. The first set of distance information can be represented by electrical impedance. The first set of distance information can be based on a physiologic impedance determined using known distances between the first electrode and the second electrode. In some embodiments, the expandable assembly can comprise at least one spline, and the first electrode and the second electrode can be attached to the at least one spline. The first set of distance information can be determined using an impedance value for circulating blood and/or tissue proximate at least the first and second electrodes.

The first electrode and the second electrode can comprise dipole mapping electrodes. The expandable assembly can comprise a first spline comprising the first electrode and a second spline comprising the second electrode, and the distance measurement assembly can produce data representing the distance between the first spline and the second spline. The first electrode can comprise a dipole mapping electrode, and the ablation catheter can comprise the second electrode, and the distance measurement assembly can produce data representing a distance between the diagnostic catheter and the ablation catheter. In some embodiments, the system can further comprise a third catheter device comprising the second electrode, and the first electrode can comprise a dipole mapping electrode, and the distance measurement assembly can produce data representing a distance between the diagnostic catheter and the third catheter device.

The diagnostic catheter can comprise at least two electrodes, and the distance measurement assembly can be configured to deliver a signal to the diagnostic catheter at least two electrodes, record a first generated signal from the diagnostic catheter at least two electrodes, and produce a first set of distance information based on the recording of the first generated signal. The diagnostic catheter plurality of dipole mapping electrodes can comprise the at least two electrodes. The first set of distance information can represent the geometric configuration of the expandable assembly.

The system can further comprise a second diagnostic catheter comprising at least one electrode, and the distance measurement assembly can be further configured to deliver a signal to the second diagnostic catheter at least one electrode, record a second generated signal from the second diagnostic catheter at least one electrode, and produce a second set of distance information based on the recording of the second generated signal.

The ablation catheter can comprise at least one electrode, and the distance measurement assembly can be further configured to deliver a signal to the ablation catheter at least one electrode, record a second generated signal, and produce a second set of distance information based on a comparison of the signal delivered to the ablation catheter at least one electrode and the recording of the second generated signal. The diagnostic catheter can comprise an electrode and the second set of distance information can comprise the distance between the ablation catheter at least one electrode and the diagnostic catheter electrode. The ablation catheter at least one electrode can comprise a first electrode and a second electrode, and the distance information can comprise the distance between the first electrode and the second electrode.

The system can further comprise a second ablation catheter comprising at least one electrode, and the distance measurement assembly can be further configured to deliver a signal to the second ablation catheter at least one electrode, record a second generated signal from the second ablation catheter at least electrode, and produce a second set of distance information based on the recording of the second generated signal.

The system can further comprise a second diagnostic catheter comprising at least one electrode, and the distance measurement assembly can be further configured to deliver a signal to the second diagnostic catheter at least one electrode, record a second generated signal from the second diagnostic catheter at least electrode, and produce a second set of distance information based on the recording of the second generated signal.

The system can further comprise at least one body surface electrode, and the distance measurement assembly can be further configured to deliver a signal to the at least one body surface electrode, record a second generated signal from the at least one body surface electrode, and produce a second set of distance information based on the recording of the second generated signal.

The system can further comprise a steerable sheath comprising an elongate shaft with a proximal end, a distal end, and a lumen therethrough, where the sheath elongate shaft can be configured to be inserted into a body and the sheath lumen can be configured to slidingly receive the diagnostic catheter shaft.

The system can further comprise a robotically manipulatable assembly. The system can further comprise a robotic assembly configured to manipulate the robotically manipulatable assembly. The system can be configured to manipulate the robotically manipulatable assembly based on an analysis of at least one of: dipole mapping information recorded by at least one dipole mapping electrode or distance information recorded by at least one ultrasound transducer. The system can be configured to manipulate the robotically manipulatable assembly based on an analysis of dipole mapping information recorded by at least one dipole mapping electrode and distance information recorded by at least one ultrasound transducer. The system can comprise a first electrode and a second electrode, and the system can be further configured to manipulate the robotically manipulatable assembly based on distance information produced by comparing a signal delivered to the first electrode to a signal recorded by the second electrode. The system can be configured to automatically manipulate the robotically manipulatable assembly, for example, the system can be configured to receive manipulation criteria from an operator, and the automatic manipulation can be performed based on the operator input information. The system can be configured to assess contact with tissue, and the robotically manipulatable assembly can be manipulated based on the contact assessment, for example the system can be configured to receive contact threshold criteria from an operator, and the manipulation can be performed based on the operator input information. The system can be configured to allow an operator to manipulate the robotically manipulatable assembly. The ablation catheter can comprise the robotically manipulatable assembly, for example where the ablation catheter comprises a steerable portion that is configured to be robotically manipulated. The diagnostic catheter can comprise the robotically manipulatable assembly, for example where the diagnostic catheter comprises a steerable portion that is configured to be robotically manipulated.

The system can further comprise an energy source configured to provide energy to the at least one ablation element of the ablation catheter. The energy source can be configured to provide an energy form selected from the group consisting of: radiofrequency energy; cryogenic energy; laser energy; light energy; microwave energy; ultrasound energy; chemical energy; and combinations of these. The diagnostic catheter can comprise at least one ablation element and the energy source can be configured to deliver energy to the diagnostic catheter at least one ablation element. The system can further comprise a second ablation catheter comprising at least one ablation element, and the energy source can be configured to deliver energy to the second ablation catheter at least one ablation element.

The system can further comprise an electrical signal source coupled to the plurality of dipole mapping electrodes. The electrical signal source can comprise a current source.

The system can further comprise an electrogram recording catheter. The diagnostic catheter can be configured to be positioned in the left atrium, and the electrogram recording catheter can be configured to be positioned in the coronary sinus. The electrogram recording catheter can comprise a catheter with a helical array of electrodes. The electrogram recording catheter can be configured to be positioned in at least one of the left atrium; a pulmonary vein; or the coronary sinus. The electrogram recording catheter can comprise a distal portion configured to be slidingly received by the diagnostic catheter shaft.

The system can further comprise a second ablation catheter. The second ablation catheter can be configured to be slidingly received by the diagnostic catheter shaft. The second ablation catheter can be of similar or dissimilar construction as the first ablation catheter.

The system can further comprise a third catheter device configured to be slidingly received by the diagnostic catheter shaft. The third catheter device can comprise a device selected from the group consisting of: a catheter with helical array of electrodes such as a lasso catheter; a pacing catheter; an energy delivery catheter such as a catheter constructed and arranged to deliver radiofrequency energy, microwave energy, cryogenic energy, laser energy and/or ultrasound energy; a drug or other agent delivery catheter such as a catheter constructed and arranged to deliver antiarrhythmic medications, stem cells, or other biologic agents; a mechanical device delivery catheter; and combinations of these. The third catheter device can comprises a mechanical device deployment catheter. The mechanical device deployment catheter can be configured to deploy a device selected from the group consisting of: robotic navigation or manipulation device, an atrial appendage closure device, a valve replacement device, a tissue biopsy device;

and combinations of these. The third catheter device can comprise a robotically manipulatable catheter device.

The system can further comprise a treatment device. The treatment device can comprise a distal portion configured to be slidingly received by the shaft of the diagnostic catheter. The treatment device can comprise a device selected from the group consisting of: a pacing device; a defibrillation device; a stent delivery device; a drug delivery device, a stem cell delivery device; and combinations of these.

In accordance with another aspect of the present disclosure, a diagnostic catheter comprises an elongate shaft comprising a distal end, where the shaft is configured to slidingly receive the distal portion of the shaft of a second catheter; an expandable assembly mounted to the diagnostic catheter shaft and configured to transition from a compacted state to an expanded state; a plurality of dipole mapping electrodes coupled to the expandable assembly; and a plurality of ultrasound transducers coupled to the expandable assembly.

The catheter can be configured to provide information selected from the group consisting of: surface unipolar voltage information; surface bipolar voltage information; surface charge density information; monophasic action potential information; anatomical geometry configuration; and combinations of these.

The catheter can be configured to be positioned in at least one of the left atrium and the left ventricle.

The catheter can further comprise a robotically manipulatable assembly. The catheter can comprise a steerable portion configured to be robotically manipulated. The catheter can comprise a shaft configured to be robotically at least one of advanced or retracted.

The expandable assembly can be positioned on the distal end of the shaft. The expandable assembly can be configured to radially expand. In some embodiments, the catheter further comprises a sheath with a distal end, and the expandable assembly can be configured to radially expand as it exits the sheath distal end.

The expandable assembly can comprise a plurality of expandable members. The plurality of expandable members can be formed of a material comprising a shape memory alloy, for example a shape memory alloy comprising Nitinol. The plurality of expandable members can be formed of a material comprising a shape memory polymer, for example a shape memory polymer comprising a triple shape acrylic.

The expandable assembly can comprise a plurality of bendable splines, where each spline comprises a proximal end and a distal end. Each spline can further comprise a set of spaced dipole mapping electrodes. The set of spaced dipole mapping electrodes can comprise at least 4 dipole mapping electrodes, or at least 6 dipole mapping electrodes, or at least 8 dipole mapping electrodes. Each spline can further comprise a set of spaced ultrasound transducers. The set of spaced ultrasound transducers can comprise at least 4 ultrasound transducers, or at least 6 ultrasound transducers, or at least 8 ultrasound transducers. Each spline can further comprise at least two of the plurality of dipole mapping electrodes and at least two of the plurality of ultrasound transducers. For example, one or more of the plurality dipole mapping electrodes can be disposed between two adjacent ultrasound transducers on each spline.

Each spline proximal end can be fixedly attached at a location proximate the diagnostic catheter elongate shaft distal end, and each spline distal end can be connected in a circumferential arrangement. The circumferential arrangement can define an opening when the expandable assembly is in an expanded state. The diagnostic catheter shaft can comprise a distal portion defining a central axis, and the opening can be relatively centered about the axis. The expandable assembly can further comprise two or more guide elements, for example two or more guide elements configured to cause a distal end of a second shaft to tend to pass through the opening.

The plurality of dipole mapping electrodes can comprise non-polarizing metals. The plurality of dipole mapping electrodes can comprise non-noble metals constructed and arranged to oxidize when in contact with at least one of blood, blood plasma, or saline solutions. The plurality of dipole mapping electrodes can comprise a coating selected from the group consisting of: a metal oxide coating; a conductive polymer coating; and combinations of these. The plurality of dipole mapping electrodes can comprise a coating constructed to be at least one of electrochemically catalytic or directly reactive with at least one of blood, blood plasma or saline solutions. The plurality of dipole mapping electrodes can further comprise an outer layer, an inner layer positioned within the outer layer, where the outer layer can comprise an impedance lowering layer and the inner layer can be configured to bond to the outer layer. The plurality of dipole mapping electrodes can comprise a polarizing metal. The plurality of dipole mapping electrodes can comprise a noble metal.

The plurality of dipole mapping electrodes can comprise a quantity equal to the quantity of the plurality of ultrasound transducers. A number of dipole mapping electrodes can be greater than a number of ultrasound transducers. Each of the plurality of dipole mapping electrodes can be disposed between two ultrasound transducers. Each of the plurality of ultrasound transducers can be disposed between two dipole mapping electrodes.

The plurality of ultrasound transducers can comprise an assembly selected from the group consisting of: single or multi-element piezoelectric ceramics; piezoelectric micro-machined ultrasound transducers (pMUT); capacitive micro-machined ultrasound transducers (cMUT); piezoelectric polymers; and combinations of these.

The diagnostic catheter shaft can comprise a braided layer. The braided layer can comprise two or more electrical conductors positioned therein. The two or more electrical conductors can comprise two or more coaxial cables. At least one conductor can be electrically connected to a dipole mapping electrode, and at least one conductor can be electrically connected to an ultrasound transducer. At least one conductor can be positioned in the braided layer in a helical pattern.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION

Figure 1A:
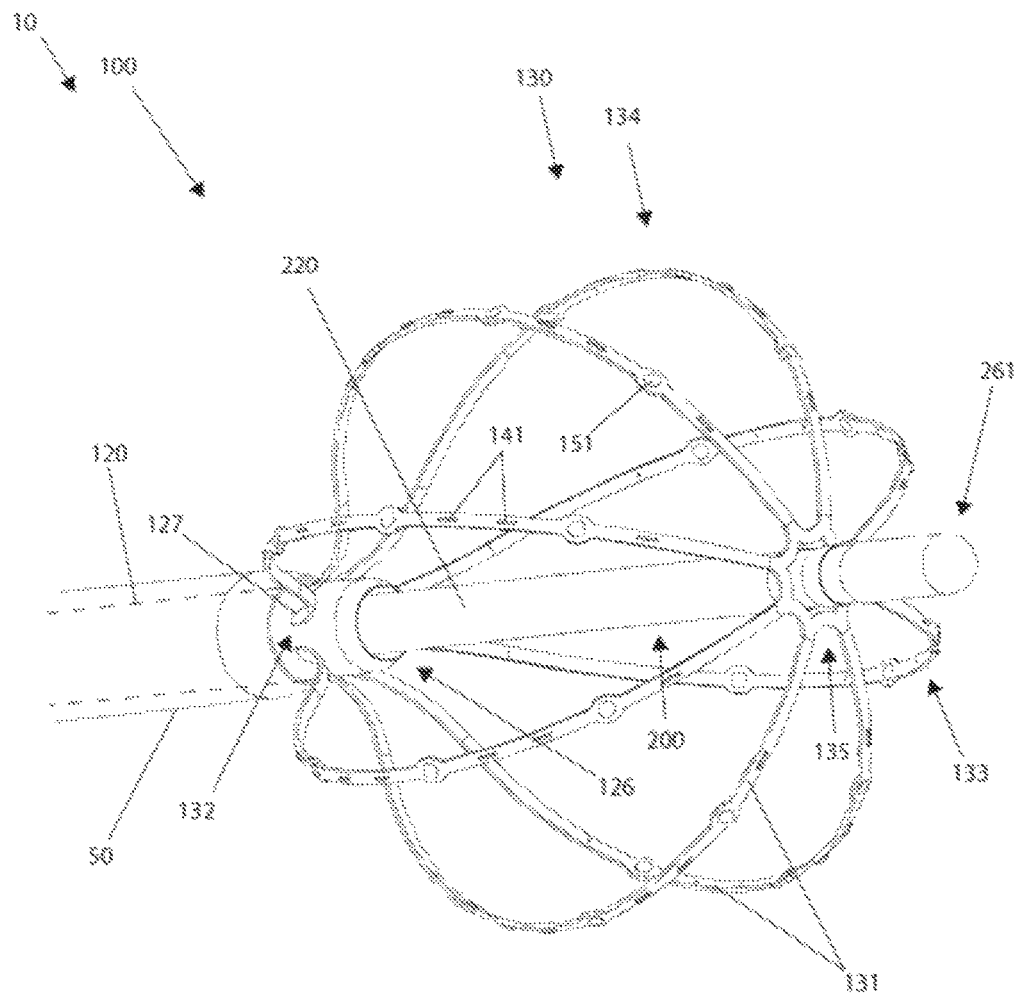
FIG. 1A is a perspective view of a system for treating a patient including an ablation catheter slidingly received by the shaft of a diagnostic catheter, in accordance with aspects of the present invention.

Various exemplary embodiments will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Exemplary embodiments are described herein with reference to cross-sectional illustrations that are schematic illustrations of idealized exemplary embodiments (and intermediate structures). As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

The catheters and other devices of the present invention can include numerous forms of diagnostic catheters such as catheters including one or more electrodes, or therapeutic catheters such as tissue ablation catheters. Catheters can be introduced percutaneously into a patient's heart, such as to record electrical activity, measure distances between structures, or deliver energy. External devices and systems can be included, such as body surface electrodes used to record electrical activity or deliver an electric signal, or visualization devices such as external ultrasound or fluoroscopic imaging systems. Any of these catheters or other devices can include one or more electrodes and/or one or more ultrasound transducers. The electrodes and/or ultrasound transducers of the present invention can be positioned at any location on the device, for example at a distal or proximal portion of the device, and can be positioned internal or external to a patient's body.

Any or all of the ultrasound transducers of the present invention can be used to measure a distance between the transducer and a surface, as is known in the art. One example includes measuring the distance between the ultrasound transducer and a wall of the cardiac chamber.

Any or all of the electrodes of the present invention can be used to record electric "signals" (e.g. voltages and/or currents) at or between the electrode locations. Recorded electric signals can be used to map electrical activity of tissue, such as when the electrode is in contact with tissue, and algorithms are used to correlate a recorded signal at one location that, for example, is not in contact with tissue, to a signal present at another location that, for example, is in contact with tissue. The mapped electrical activity can be further processed (e.g. in terms of sources of charge and charge density and correlated with various physiologic parameters related to the function of the heart) and the mapped electrical activity and other recorded and calculated information can be provided visually to one or more operators of the system of the present invention.

Any or all of the electrodes of the present invention can be used to deliver and/or record electric signals that are generated by the system. Such delivered signals can be emitted from any one or more electrodes, and can be delivered between any two or more electrodes. Recorded signals can comprise a signal present at a single electrode location or at multiple electrode locations (e.g. a signal representing a comparison of two or more signals present at two or more electrode locations). Recorded signals can be measured, for example, synchronously or asynchronously in terms of voltage and/or current. Recorded signals can be further processed in terms of, for example, resistive and reactive components of impedance and/or the combined magnitude of impedance with any original or processed signal "values" (e.g. those represented by a parameter selected from the group consisting of: instantaneous amplitude; phase; peak; Root-Mean-Square; demodulated magnitude; and combinations of these).

The terms "map" and "mapping" shall include "electrical map", "electrical mapping", "anatomical map", "anatomical mapping", "device map" and "device mapping", each of which is defined herebelow.

The terms "electrical map" and "electrical mapping" shall include recording, processing and/or displaying electrical information, such as electrical information recorded by one or more electrodes of the present invention. This electrical information includes but is not limited to: cardiac or other tissue voltage measurements; cardiac or other tissue bipolar and/or unipolar electrograms; cardiac or other tissue surface charge data; cardiac or other tissue dipole density data; cardiac or other tissue monophasic action potentials; and combinations of these.

The terms "anatomical map" and "anatomical mapping" shall include recording, processing and/or displaying anatomical information, such as anatomical information provided by one or more ultrasound transducers of the present invention and/or one or more electrodes of the present invention. This anatomical information includes but is not limited to: two or three dimensional representations of tissue such as one or more chambers of a heart; tissue wall thicknesses such as the thickness of an atrial or ventricular wall; distance between two tissue surfaces; and combinations of these. In some embodiments, a dipole density map is provided by using information provided by multiple electrodes and multiple ultrasound transducers, such as is described in Applicant's co-pending international application, Serial Number PCT/US2012/028593, entitled Device and Method For the Geometric Determination of Electrical Dipole Densities on the Cardiac Wall, the entirety of which is incorporated herein.

The terms "device map" and "device mapping" shall include recording, processing and/or displaying of device distance information such as information comprising the distance between a device or device component and another object, such as tissue or another device or device component.

Any pair of electrodes of the present invention can be constructed and arranged to provide distance information, such as the distance between that pair of electrodes, or the distance between one of the electrodes and one or more proximate components (e.g. a component at a known distance from one or both of the electrodes in the pair). By delivering and recording an electric signal between electrodes of known separation distances, the signal can by processed and/or calibrated according to one or more known separation distances (e.g. the separation distance between two electrodes fixedly mounted to a rigid structure at a pre-determined distance). Calibrated signal values can be combined across adjacent sets of electrode pairs to accurately estimate the distance between any pair (e.g. any arbitrary pair of electrodes on any one or more devices of the system) of electrodes for which the separation distance is not known. Known and calculated separation distances can be used as "reference" electrodes and combined to triangulate the unknown position of one or more "marker" electrodes, such as an electrode positioned on the present invention or on a separate or external device and positioned proximate the present invention. The process of triangulation can be used to dynamically localize the three-dimensional position of any or all of the electrodes either individually and/or as a combined entity in three dimensional (3D) space. Numerous distance measurement techniques are described in detail in reference to FIGS. 2A and 2B herebelow.

Further, any or all electrodes of the present invention can be used to deliver electric energy, such as radiofrequency energy.

Referring now to FIG. 1A, a perspective view of the distal portion of a system for diagnosing and/or treating a heart arrhythmia, such as atrial fibrillation and/or ventricular tachycardia, is illustrated. The system includes an ablation catheter slidingly received by the shaft of a diagnostic catheter. System 10 includes diagnostic catheter 100 which is constructed and arranged for insertion into a body location, such as the chamber of a heart. Catheter 100 includes shaft 120, typically constructed of sufficiently flexible material to allow insertion through the tortuosity imposed by the patient's vascular system. On the distal portion of shaft 120 is an expandable assembly 130 which includes a plurality of electrodes 141 coupled thereon. Additionally, a plurality of ultrasound transducers 151 are coupled to expandable assembly 130. System 10 further includes ablation catheter 200, which includes shaft 220. Shaft 220 includes at least one ablation element 261, positioned at the tip or otherwise on a distal portion of shaft 220. Ablation element 261 is constructed and arranged to deliver energy to tissue, such as when ablation catheter 200 is attached to a source of energy as is described in reference to FIG. 6 herebelow.

Shaft 120 includes a lumen 126 traveling from at least a proximal portion of shaft 120 (e.g. from a handle, not shown but typically positioned on shaft 120's proximal end) to a distal portion of shaft 120 (e.g. to shaft 120's distal end). Shaft 220 of ablation catheter 200 and lumen 126 of diagnostic catheter 100 are constructed and arranged to allow shaft 220 of ablation catheter 200 to be slidingly received by lumen 126. Lumen 126 can be further configured to slidingly receive additional catheters or other elongate devices, such as prior to insertion of diagnostic catheter 100 into a body, or after diagnostic catheter 100 has been inserted into a body.

Diagnostic catheter 100 can be used for mapping tissue such as an organ or portion of an organ (e.g. a portion of a heart wall). Three dimensional anatomical mapping information collected by diagnostic catheter 100 can be used by system 10 to create a three dimensional display of an anatomical location of which at least a portion is to be treated by ablation catheter 200. Diagnostic catheter 100 can be coupled to a computer system, not shown but configured to display anatomical mapping information generated by diagnostic catheter 100 such as volumes, locations, shapes, contours, and movement of organs, nerves, and other tissue within the body. Diagnostic catheter 100 can be coupled to the computer system to display the electrical mapping information generated by diagnostic catheter 100, such as to display dipole mapping or other information as has been described above. Additionally, the location of ablation catheter 200 or other inserted devices can be displayed, such as their position relative to tissue or diagnostic catheter 100. For example, diagnostic catheter 100 can be used to map the heart, while ablation catheter 200 can be directed to a tissue location in the heart targeted for treatment (e.g. targeted for treatment based on information provided by diagnostic catheter 100). For example, ablation catheter 200 can be configured to ablate cardiac tissue to treat a patient suffering from a cardiac arrhythmia, such as atrial fibrillation, atrial flutter, supraventricular tachycardias (SVT), Wolff-Parkinson-White syndrome, and ventricular tachycardias (VT). An ablation catheter will be described herein as a form of a treatment device for purposes of conveying aspects of the invention, but a different type of treatment device (e.g., a pacing device; a defibrillation device; a stent delivery device; a drug delivery device, a stem cell delivery device, or the like) can be used in other embodiments in combination with diagnostic catheter 100. In some embodiments, one or more of these treatment devices is inserted through a lumen of diagnostic catheter 100.

In some embodiments, system 10 is configured to access the left atrium of the patient while utilizing a single transseptal puncture through which all the catheter components of system 10 access the left atrium (and subsequently the left ventricle in some cases). In other embodiments, system 10 is configured to access the left ventricle of the patient while utilizing a single crossing of the aortic valve through which all the catheter components of system 10 access the left ventricle (and subsequently the left atrium in some cases). System 10 can include sheath 50, for example a standard access sheath, such as a standard transseptal access sheath. In some methods, sheath 50 is inserted through the atrial septum and into the left atrium, followed by the insertion of diagnostic catheter 100 through a lumen of sheath 50. Subsequently, ablation catheter 200 is inserted through lumen 126 of diagnostic catheter 100. In other methods, sheath 50 is inserted into the left atrium, followed by the simultaneous insertion of diagnostic catheter 100 and ablation catheter 200 (e.g. diagnostic catheter 100 is inserted with ablation catheter 200 residing at least partially within lumen 126). In some embodiments, sheath 50 can include a steerable sheath. Shaft 120 comprises a diameter along the majority of its length such as to be slidingly received by sheath 50. In some embodiments, shaft 120 comprises a diameter less than or equal to 15 Fr. In some embodiments, diagnostic catheter 100 and/or ablation catheter 200 are steerable, such as is described in reference to FIGS. 3 and 6 herebelow, so as manual, semi-automatic or automatic steering can be performed by an operator and/or a robotic control assembly of system 10.

Diagnostic catheter 100 can be positioned in the left atrium and can provide information selected from the group consisting of: electrical information such as surface charge information; anatomical geometry information such as heart wall surface information or heart wall thickness information; other physiologic and anatomical information such as those described herein; and combinations of these. Shaft 120 of diagnostic catheter 100 can be configured to be inserted into the heart via the venous system, for example a vein in a leg or a vein in a neck. Shaft 120 can include a braid within its outer and inner surfaces, not shown but typically a braid of plastic or metal fibers that enhance the structural integrity and performance of shaft 120. In some embodiments, the braid of shaft 120 can include conductors, such as is described in reference to FIG. 3 herebelow.

As described above, diagnostic catheter 100 of FIG. 1A includes lumen 126 extending from a proximal portion to a distal portion of shaft 120, for example from a proximal end to a distal end of shaft 120 so as to allow a separate catheter or other elongate device to be inserted therethrough, such as ablation catheter 200, as shown. Alternatively or additionally, the inserted catheter or other elongate device can include a diagnostic catheter such as a diagnostic catheter configured to record signals from a location selected from the group consisting of: the left atrium; the right atrium; the Bundle of HIS; the right ventricular apex; a pulmonary vein; the coronary sinus. Alternatively or additionally, the inserted catheter can comprise another catheter device, such as catheter device 700 described in reference to FIG. 6 herebelow.

Diagnostic catheter 100 of FIG. 1A includes expandable assembly 130, which is positioned at the distal end of shaft 120. As illustrated, expandable assembly 130 includes an array of splines 131, each spline 131 having proximal segment 132, middle portion 134, and distal segment 133. Proximal segment 132 of each spline 131 connects to shaft 120, via connection point 127, described in detail in reference to FIG. 2 herebelow. The distal ends of each spline 131 connect in a circumferential ring configuration to form opening 135. Opening 135 allows a device to pass therethrough such as a device inserted into lumen 126, for example shaft 220 of ablation catheter 200. In some embodiments, expandable assembly 130 can include one or more guide elements configured to guide a device through opening 135, guide elements not shown but described in detail in FIGS. 7A-B herebelow.

Expandable assembly 130 is constructed and arranged to be positioned in the expanded shape shown in FIG. 1A. The expanded geometry of assembly 130, including at least two or more splines 131 in an expanded or partially expanded state (hereinafter "expanded state"), can be described as a "basket" having a substantially hollow center and spaces between adjacent splines 131. In the illustrated embodiment, the basket is spherical, but can include any suitable shape, for example an ellipsoid. Thus, in other embodiments, assembly 130 can comprise different shapes or combination of shapes, such as an array of splines 131 where two or more splines 131 comprise similar or dissimilar shapes, dimensions or configurations. In some embodiments, two or more splines 131 include a varied radius of curvature.

Expandable assembly 130 can be biased in an expanded or non-expanded state. In an example, assembly 130 can be self-expanding such that splines 131 are resiliently biased in the curved geometry shown in FIG. 1A. Assembly 130 can automatically expand when assembly 130 exits the distal end of sheath 50, such as by advancement of shaft 120 and/or retraction of sheath 50. Alternatively, assembly 130 can be manually expanded, for example via retraction of a rod 129 that slides within shaft 120 and is connected to distal end of assembly 130, as described in detail in reference to FIG. 2 herebelow.

Splines 131 can be constructed of a material selected from the group consisting of: one or more thermoplastic polymers such as polyether block amide, polyurethane and/or polyether ether ketone; one or more of thermoset polymers such as silicon and/or tetrafluoroethylene; one or more metals such as stainless steel and/or shaped memory alloys such as nickel titanium alloy; one or more shape memory polymers such as triple shape acrylic; and combinations of these. Generally, any of a number of materials or compositions that are biocompatible, flexible or bendable, and possess any necessary application specific electrical properties can be used for splines 131.

Splines 131 can include one or more electrodes 141 and/or one or more ultrasound transducers 151 arranged in any combination. For example, in some embodiments, one or more of the following configurations is included: each spline 131 includes at least four, six or eight electrodes 141; each spline 131 includes at least four, six or eight ultrasound transducers 151; and combinations of these. In some embodiments, at least one electrode 141 is positioned between two ultrasound transducers 151 on a single spline 131. In some embodiments, at least two electrodes 141 are positioned between two ultrasound transducers 151 on a single spline 131.

Each spline 131 can include a similar or dissimilar arrangement of electrodes 141 and/or ultrasound transducers 151 as an adjacent spline 131 or any other spline 131 in assembly 130. In some embodiments, assembly 130 includes eight splines 131, where each spline 131 can include two to eight electrodes 141 and two to eight ultrasound transducers 151. In some embodiments, assembly 130 includes six splines 131, where each spline 131 can include eight electrodes 141 and eight ultrasound transducers 151. In some embodiments, one or more splines 131 include a number of electrodes 141 that comprises a quantity within one of the quantity of ultrasound transducers 151 that are included on that spline 131. For example, a spline 131 can include seven electrodes 141 and either six or eight ultrasound transducers 151. In some embodiments, a set of electrodes 141 and ultrasound transducers 151 can be arranged in an alternating arrangement, such that one or more single ultrasound transducers 151 lies between two electrodes 141. In some embodiments, some sets of electrodes 141 and ultrasound transducers 151 can be arranged such that one or more single electrodes 141 is positioned between two ultrasound transducers 151.

Electrodes 141 can be configured to record electric signals such as voltage and/or current signals. System 10 can utilize the recorded signals to produce electrogram information; dipole mapping information; distance information such as the distance between any device and/or component of system 10; and other information or combinations of information described in detail herein. Any or all electrodes 141 of system 10 can comprise a dipole mapping electrode, such as an electrode with a impedance or other electrical property configured to provide information related to surface charge or other dipole mapping parameter. In some embodiments, the electrodes 141 are of sufficiently low impedance, such as in the range less than 10,000 ohms, such as to achieve high-fidelity recording of signal frequencies greater than or equal to 0.1 Hz. In some embodiments, one or more electrodes 141 include an iridium oxide coating, such as to reduce the impedance of electrodes 141. Alternatively or additionally, numerous forms of coatings or other treatments can be included with one or more electrodes 141, such as a platinum black coating or a carbon nanotube layer. In addition or as an alternative to recording electric signals, electrodes 141 can be constructed and arranged to deliver electric energy, such as radiofrequency energy. In some embodiments, diagnostic catheter 100 can deliver therapy, such as an ablation therapy delivered to tissue, in addition to its function as a diagnostic catheter, e.g. providing electrical, anatomical and/or device mapping information. In some embodiments, one or more electrodes 141 each comprise one or more coils, such as when the one or more coils are configured to create one or more magnetic fields.

Electrodes 141 can include various materials such as non-polarizing metals and/or polarizing metals. In some embodiments, one or more electrodes 141 comprise at least one non-noble metal such that electrodes 141 oxidize when in contact with at least one of blood, blood plasma or saline solutions. In some embodiments, electrodes 141 include a coating, for example a coating selected from the group consisting of: a metal oxide coating; a conductive polymer coating; and combinations of these. In some embodiments, one or more electrodes 141 can include an outer layer and an inner layer, such as when the outer layer comprises an impedance lowering coating or other layer and the inner layer comprises a layer configured to bond the outer layer to the metallic and/or other remaining portion of the one or more electrodes 141.

Ultrasound transducers 151 can be configured to record distance information such as the distance between any device and/or component of system 10 and tissue such as cardiac wall or other solid tissue. Ultrasound transducers 151 can include a construction comprising: single or multi-element piezoelectric ceramics; piezoelectric micro-machined ultrasound transducers (pMUT); capacitive micro-machined ultrasound transducers (cMUT); piezoelectric polymers; and combinations of these.

In some embodiments, diagnostic catheter 100 can include a multi-layer or laminate construction, for example where shaft 120 includes a tube inside of another tube; where shaft 120 includes a liner such as a lubricous liner such as PTFE; where shaft 120 includes a braided construction such as a braid positioned between two layers of shaft 120; and combinations of these. In some embodiments, diagnostic catheter 100 can be steerable, for example via the incorporation of a pull wire and anchor as shown and described in reference to FIG. 3 herebelow. Typically, diagnostic catheter shaft 120 outer diameter is less than 15 Fr.

Ablation catheter 200 of FIG. 1A includes ablation element 261 positioned on shaft 220, for example on a distal portion or the distal tip of shaft 220. Ablation element 261 can include a functional element selected from the group consisting of: one or more electrodes; a vessel configured to deliver cryogenic energy; a laser diode; an optical fiber configured to deliver ablative energy; a microwave energy delivery element; an ultrasound energy delivery element; a drug, stem cell, or other agent delivery element; a mechanical or other ablation device delivery element; and combinations of these. In the case where ablation element 261 includes one or more electrodes, the electrodes can include electrodes constructed and arranged to deliver radiofrequency (RF) energy. In the case of multiple electrodes, the electrodes can be configured for bipolar RF energy delivery. In some embodiments, ablation element 261 includes an array of elements such as in one or more of the component array configurations shown in FIG. 6. Ablation catheter 200 can be operably connected to a device configured to deliver energy to ablation element 261, such as energy delivery unit 400 of FIG. 6. Typical energy delivered by ablation element 261 comprises an energy selected from the group consisting of: electromagnetic energy such as radiofrequency energy; cryogenic energy; laser energy; light energy; microwave energy; ultrasound energy; chemical energy; and combinations of these.

Figure 1B:
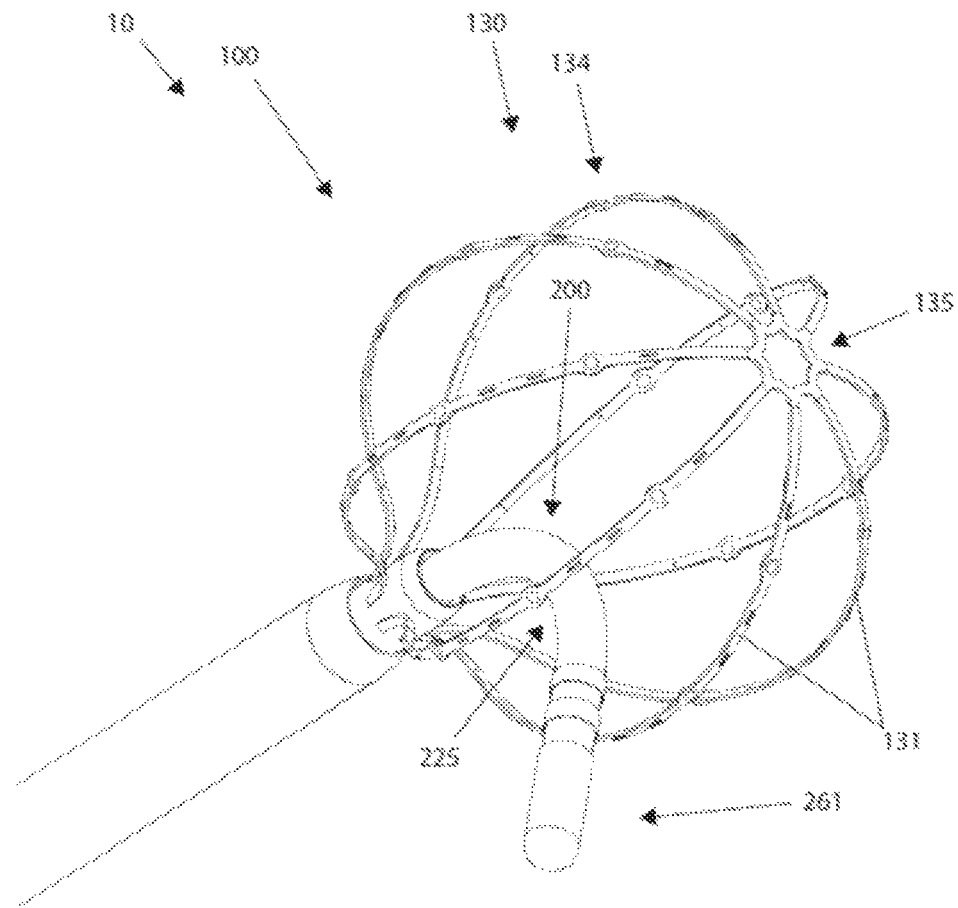
FIG. 1B is a perspective view of the system of FIG. 1A, where the ablation catheter is steered into a bent configuration, in accordance with aspects of the present invention.
Figure 3:
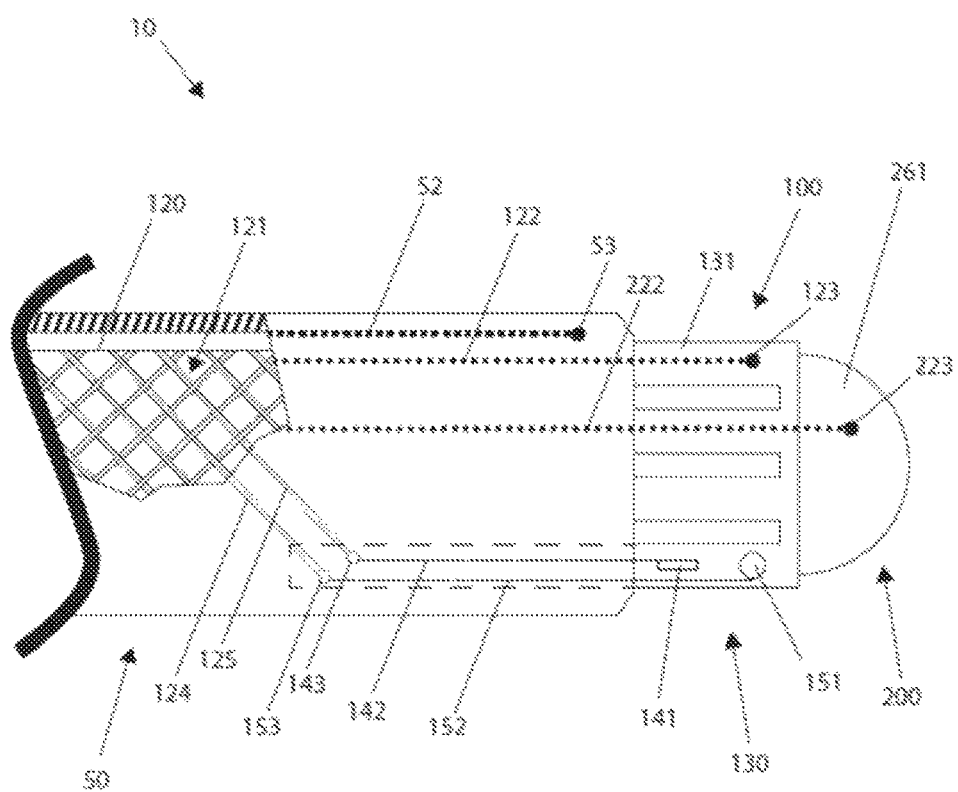
FIG. 3 is a side view of the system of FIG. 1A where the diagnostic catheter is retracted into a sheath, in accordance with aspects of the present invention.

Similar to diagnostic catheter 100 and sheath 50, ablation catheter 200 can be steerable, such as via a pull wire and anchor as described in reference to FIG. 3 herebelow. Referring now to FIG. 1B, distal portion 225 of ablation catheter 200 has been steered in the curved geometry shown to cause ablation element 261 to exit expandable assembly 130 of diagnostic catheter 100, passing between two middle portions 134 of two splines 131. Ablation catheter 200 can be steered and advanced by an operator such as a clinician, so as to exit at any opening of the expandable assembly 130, including the space between two splines 131 or through opening 135, such as to be further advanced to contact and ablate cardiac tissue.

Figure 2:
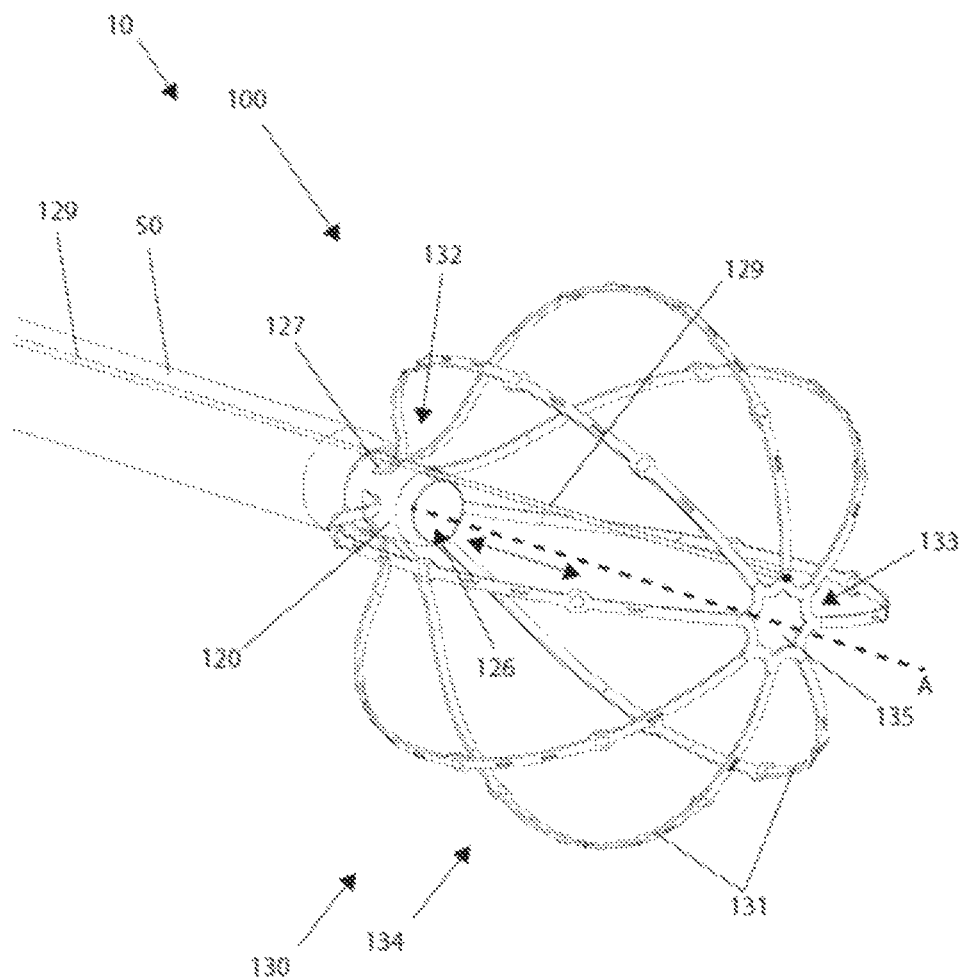
FIG. 2 is a perspective view of the system of FIGS. 1A and 1B, without the ablation catheter and including a push rod, in accordance with aspects of the present invention.

Referring now to FIG. 2, a perspective view of the distal portion of the system of FIGS. 1A and 1B is illustrated, including a push rod operably attached to expandable assembly 130. System 10 includes diagnostic catheter 100 and ablation catheter 200. Diagnostic catheter 100 comprises an elongate shaft 120 which includes lumen 126 exiting its distal end. Ablation catheter 200, which has been removed for clarity, is configured to be slidingly received by lumen 126. Diagnostic catheter 100 includes push rod 129, typically a solid tube or hypotube slidingly received within a wall or a lumen of shaft 120, that can be used to expand or collapse (i.e. un-expand or compact) expandable assembly 130. Push rod 129 can be operably attached to a handle, not shown but typically a handle including one or more controls used to advance or retract push rod 129 and/or steer one or more catheter shafts. In some embodiments, retracting rod 129 causes assembly 130 to expand (e.g. the backward force applied on the distal end of assembly 130 by rod 129 causes splines 131 to bow), and advancing rod 129 causes assembly 130 to collapse (e.g. the forward force applied on the distal end of assembly 130 by rod 129 causes splines 131 to straighten).

As illustrated in FIG. 2, expandable assembly 130 includes an array of splines 131, each spline 131 having proximal segment 132, middle portion 134 and distal segment 133. Distal segments 133 of each spline 131 connect in a circumferential ring configuration to form opening 135, which is relatively orthogonal to and relatively centrally positioned about axis "A", which comprises the central axis of the distal portion of shaft 120. Opening 135 allows the distal portion of a shaft of a device to pass therethrough, such as a device inserted into lumen 126, for example shaft 220 of ablation catheter 200 of FIGS. 1A and 1B. Proximal segment 132 of each spline 131 connects to shaft 120 via connection points 127. A mechanical attachment can be made between any spline 131 and shaft 120 at connection points 127, such as an attachment comprising a compression fitting or adhesive. Any spline 131 can be attached to shaft 120 at connection point 127 via a bonding process, such as a thermal bonding process where a spline 131 is positioned in the wall of shaft 120 or when shaft 120 comprises two polymer coaxial tubes and spline 131 is thermally set between the tubes. Alternatively or additionally, adhesive bonds, mechanical crimps or and/or other bonds can be used. Proximal segments 132 are convex with respect to central axis "A" of the distal portion of shaft 120. Proximal segments 132 can transition to middle portions 134 through an inflection point, such that middle portions 134 and distal segments 133 are concave with respect to axis "A". In some embodiments, the radius of curvature of proximal segment 132 ranges from approximately 0.01 mm to 25 mm, or larger. When proximal segments 132 engage the lumen of sheath 50, such as while shaft 120 is being retracted, a compressing force is applied to proximal segments 132 by sheath 50, initiating the radial compression of assembly 130. Continued retracting of shaft 120 causes assembly 130 to be fully captured within sheath 50 and maintained in an unexpanded state. The convexity of proximal segments 132 can be chosen to allow smooth capture of assembly 130 by sheath 50, avoiding any undesired threshold forces required to initiate the radial compression of assembly 130. Other configurations for proximal segments 132 can be used to facilitate a smooth transition from the expanded state to the unexpanded, captured state. In some embodiments, push rod 129 can be partially advanced, such as to partially collapse expandable assembly 130, initiating radial compression of assembly 130, thus facilitating an easier capture of splines 131 by sheath 50.

Figure 2A:
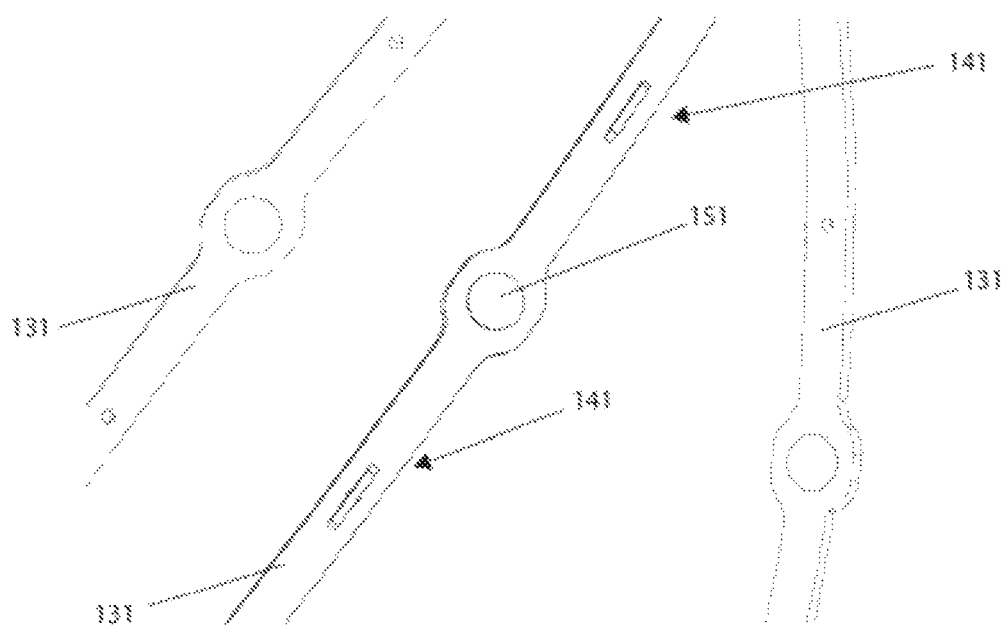
FIG. 2A is a magnified view of a portion of a spline of the diagnostic catheter of FIG. 2, including one ultrasound transducer and two adjacent electrodes, in accordance with aspects of the present invention.

Referring now to FIG. 2A, a magnified view of a portion of a spline of the diagnostic catheter 100 of FIG. 2 is illustrated, including one ultrasound transducer and two adjacent electrodes. In some embodiments, diagnostic catheter 100 includes an equal number of ultrasound transducers 151 and electrodes 141, such as an array comprising forty-eight ultrasound transducers 151 and forty-eight electrodes 141.

In some embodiments, relative positions of splines 131, electrodes 141, and ultrasound transducers 151 of expandable assembly 130 are of known values, such as when expandable assembly 130 is in a pre-configured "biased" state (e.g. a resiliently biased, fully expanded state with no forces applied). These known values can be correlated to a 3D coordinate system, such as a Cartesian coordinate system; a spherical coordinate system; and/or a coordinate system with an origin at the center of the expandable array or any location. The origin of a coordinate system can be used to map the location of one or more of: one or more components of diagnostic catheter 100 such as one or more splines 131, one or more electrodes 141 or one or more ultrasound transducers 151; one or more components of ablation catheter 200 of FIGS. 1A and 1B such as ablation element 261; one or more components of a separate device inserted into the patient; one or more components of a separate device external to the patient; one or more portions of the patient's anatomy. Other portions of diagnostic catheter, as well as anatomical features measured by diagnostic catheter 100, can be located at a useful position for performing a medical procedure, such as at the distal end of shaft 120, the distal tip of expandable assembly 130, the geometric center of expandable assembly 130, any electrode 141 or ultrasound transducer 151, or any other useful location.

In some embodiments, diagnostic catheter 100 utilizes three or more electrodes 141 (e.g. any three electrodes 141) as a reference. The three or more electrodes 141 can be used to triangulate the position of a marker electrode, such as an electrode on a separate device and positioned proximate expandable assembly 130. Each of the reference electrodes can be configured to emit an electric signal, with the three signals comprising three similar waveforms with the exception of a phase shift of 120° between them. A marker electrode can record a combined summation of the three phase shifted signals. This combined signal can be used (e.g. by one or more components of a system such as system 10 of FIG. 6 herebelow) to determine the position of the marker electrode in relation to the three electrodes, such as by using one or more triangulation algorithms. For example, if the marker electrode is at a geometric center of the three electrodes, the resultant electric signal will be zero. Non-zero readings are analyzed to determine the distance from each reference electrode to the marker electrode. Precision of marker electrode position can be improved by having additional electrodes 141 (e.g. four or more) emit a signal to be recorded by the marker electrode with values to be processed by a positioning algorithm.

Figure 6:
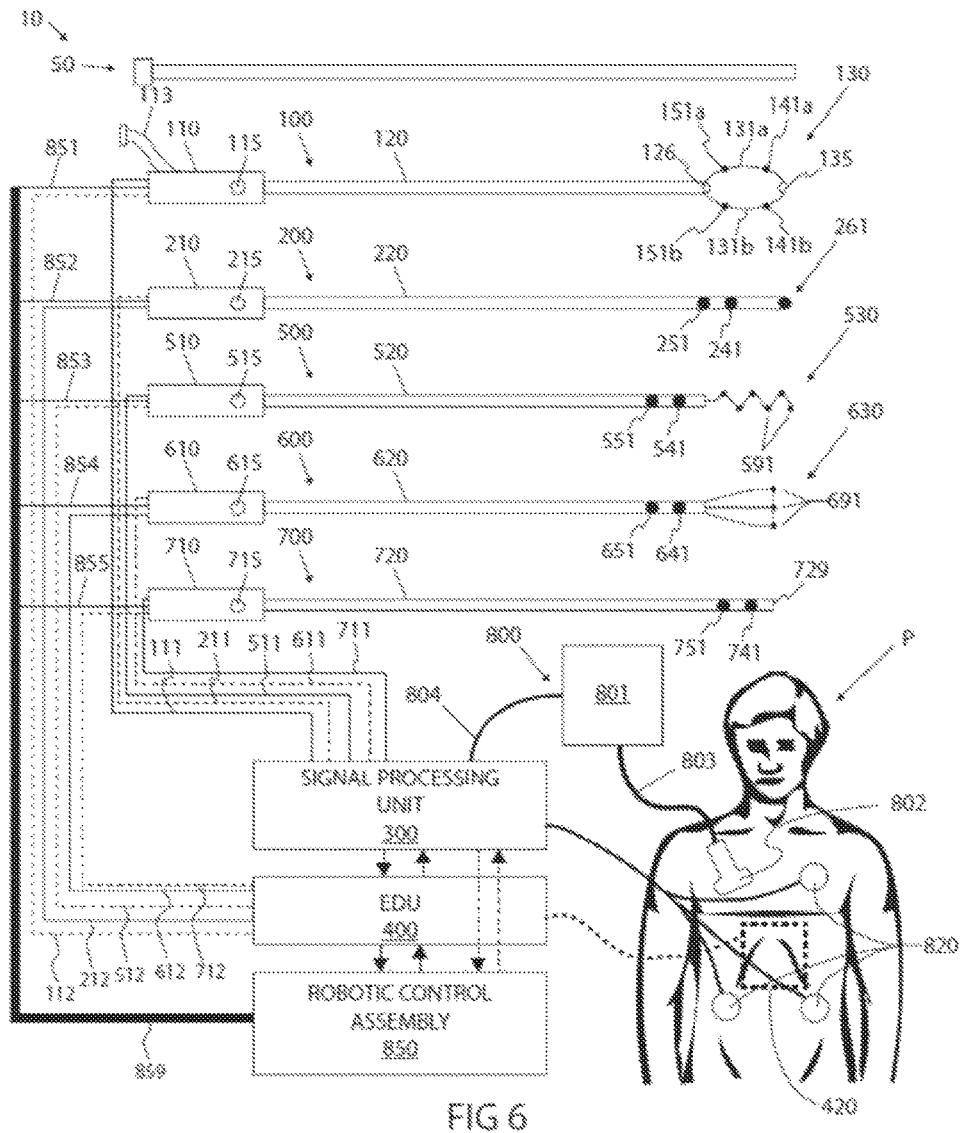
FIG. 6 is a schematic of an embodiment of a mapping and ablating system, in accordance with aspects of the present invention.

In some embodiments, three or more reference electrodes emit an electric signal, such as an electric signal provided by a component of a system, such as system 10 of FIG. 6 described herebelow. Such reference electrodes can be located in various locations, such as a location selected from the group consisting of: on diagnostic catheter 100; on an ablation catheter such as ablation catheter 200 of FIGS. 1 and 6 described herein; on one or more separate devices, such as one or more separate devices proximate expandable assembly 130; on one or more locations on the surface of the body; and combinations of these. Each reference electrode can sequentially emit a signal at the same frequency or simultaneously emit signals at different frequencies. Three or more marker electrodes record signals with values that differ in logarithmic-proportion to the separation distance between the reference electrodes and the marker electrodes. A set of three or more such marker electrodes can be comprised of any electrode 141 located on diagnostic catheter 100 or any two or more of any electrodes 141 located on diagnostic catheter 100 in combination with any one or more electrodes located on one or more separate devices positioned proximate expandable assembly 130. Recorded differences in signal-values by the marker electrodes can be combined to determine the position of the marker electrodes in relation to the reference electrodes, such as by using one or more triangulation algorithms. For example, if two or more marker electrodes are equidistant from any reference electrode, the corresponding recorded signal-values on each marker electrode will be equal in magnitude. Conversely, the values of the recorded signals will be unequal to each other in logarithmic-proportion to the amount by which each marker-electrode-to-reference-electrode separation distances are unequal. By combining the recorded signal-values with a geometric polyhedron connecting each individual reference electrode and the marker electrodes (e.g. a tetrahedron in the case of one reference electrode and three marker electrodes), the volume of the polyhedron can be analyzed to triangulate the position of the marker electrodes. Precision of the marker electrode positions can be improved by having additional neighboring sets of reference and marker electrodes that emit and record signals, respectively, and by similarly analyzing the associated sets of polyhedral volumes and combining the results of triangulation.

In some embodiments, an electric signal is delivered between two reference electrodes (i.e. emitted from a first electrode and "returned" to a second electrode), such as by a component of system, such as system 10 of FIG. 6 described herebelow. Such reference electrodes are comprised of any two of electrodes 141 located on diagnostic catheter 100 or any one of electrodes 141 located on diagnostic catheter 100 in combination with any electrode located on any separate device positioned proximate expandable assembly 130 or on any electrode located on the body surface. Three or more marker electrodes located between and proximate the two reference electrodes record signals with values that differ in logarithmic-proportion to the separation distance between each of the two reference electrodes and the marker electrodes. Any three or more such marker electrodes are comprised of any electrode 141 located on diagnostic catheter 100 or any two or more of any electrode 141 located on diagnostic catheter 100 in combination with any one or more electrodes located on one or more separate devices positioned proximate expandable assembly 130. Recorded differences in signal values can be combined to determine the position of the marker electrodes in relation to the resultant electric field generated by the signal delivered between the two reference electrodes. One or more geometric shape algorithms can be used for which the recorded signal values comprise shape parameters that conform to the geometric shape of the resultant electric field between and proximate all of the marker electrodes (e.g. such parameters that quantify how much the shape of the resultant electric field is spheroidal, oblate, prolate, eccentric, skewed, rotated and/or, offset). Precision of the marker electrode determined positions can be improved by increasing the number of marker electrodes that are used to parameterize the shape of the resultant electric field and/or by using additional unique neighboring pairs of reference electrodes to generate the resultant electric field across unique spans of the 3D space between and proximate the marker electrodes. The resultant marker field-values are recorded, the associated sets of resultant electric field shapes are parameterized, and the parameters are combined into a common resultant shape. Signals of one frequency are applied sequentially between multiple reference electrode-pairs and signals with different frequencies can be applied simultaneously.

In any embodiment, one or more marker electrodes can comprise an ablation element (e.g. to deliver RF energy), or it can be at a known position relative to an ablation element or other component of a device of a system, such as system 10 of FIG. 6 described herebelow.

Figure 2B:
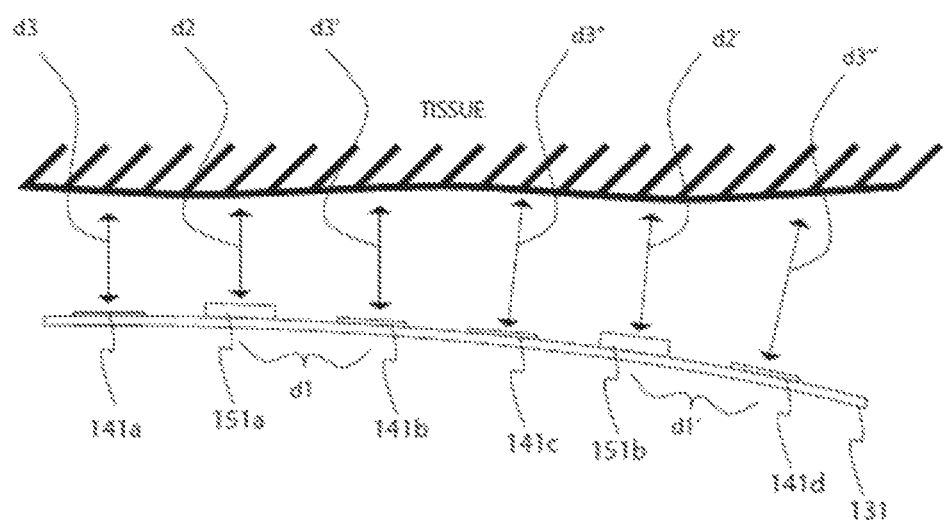
FIG. 2B is a side view of the portion of the spline of FIG. 2A disposed in a body, in accordance with aspects of the present invention.

Referring now to FIG. 2B, a side view of a segment of a spline disposed proximate to tissue is illustrated. Spline 131 is positioned proximate tissue ("TISSUE") and includes ultrasound transducers 151*a* and 151*b* as shown. Spline 131 further includes electrodes 141*a*, 141*b*, 141*c* and 141*d* as shown. Ultrasound transducers 151*a*, 151*b* can be used to provide distance information, such as the distance between each ultrasound transducer 151*a*, 151*b* and TISSUE. This distance information can be used to determine the distance between one or more electrodes 141*a*, 141*b*, 141*c*, 141*d* and TISSUE, for example by using the known distance between one or more electrodes 141*a*, 141*b*, 141*c*, 141*d* and one or more ultrasound transducers 151*a*, 151*b*, as well as a known or measured shape of spline 131. That is, the distance between any ultrasound transducer and any electrode (e.g. d1 or d1' as shown) is known or can be calculated by the system of the present invention (e.g. a calculation to account for distance changes due to bending of splines 131). Accordingly, a distance between any ultrasound transducer and TISSUE can be determined according to traditional ultrasound algorithms, for example the distances between ultrasound transducer 151*a* and 151*b* and TISSUE, represented by d2 and d2', respectively. As a result, a distance between any electrode and TISSUE can be calculated, for example the distance between electrodes 141*a*, 141*b*, 141*c* and 141*d* and TISSUE, represented by d3, d3', d3", and d3'", respectively.

If one or more forces are imparted on any spline 131, the spline can change shape. Alternatively or additionally, an imparted force on any spline 131 can cause that spline 131 to move in relation to another spline 131. Systems of the present invention can be constructed and arranged to measure these geometric changes to one or more splines 131. In some embodiments, electrical information can be collected by one or more electrodes 141 to measure one or more distances, and one or more algorithms of system 10 use the one or more measured distances to determine a geometric configuration of one or more splines 131. In some embodiments, a current is applied between any two electrodes 141, and the distance between the two electrodes 141 can be determined, such as with one or more algorithms to determine a distance, as is described in detail in reference to FIG. 2A hereabove.

Distance information can be used by one or more algorithms of system 10 to derive the real-time shape or relative positioning of one or more splines 131. The shape of a spline 131 and the distance between two electrodes 141 positioned on spline 131 is known, when spline 131 is in an equilibrium (e.g. resiliently biased) state. Measurement of a change to the equilibrium separation distance between two electrodes 141 positioned on a single spline 131 can be used by an algorithm of system 10 to determine the change in shape to the spline 131 as one or more forces are applied (e.g. as a spline 131 is pressed against a heart wall). In some embodiments, increased bowing of a spline 131 can cause the electrode 141 separation distance to decrease, and straightening of a spline 131 can cause the electrode 141 separation distance to increase, each in a predictable manner. Similarly, when an array of splines 131 are in an equilibrium state, the distance between a first electrode 141 on a first spline 131 and second electrode 141 on a second spline 131 is also known. Measurement of a change in the separation distance between these two electrodes 141 positioned on two splines 131 can be used to determine a change in relative positioning of the two splines 131 as one or more forces are applied (e.g. as a spline 131 is pressed against a heart wall).

Similarly, the distance between any two electrodes positioned on any two separate devices can be determined by an algorithm of system 10, such as the distance between one or more portions of diagnostic catheter 100 and one or more portions of ablation catheter 200, each described in reference to FIGS. 1 and 6. Another algorithm of system 10 can include measuring the distance between an electrode positioned on diagnostic catheter 100 and an electrode positioned on a third catheter device such as catheters 500 and 600 described in FIG. 6 herebelow. This measurement can be repeated between any two electrodes positioned on any device, at any time during the clinical procedure. This distance information can be useful to determine the geometry of an expandable assembly, such as expandable assembly 130 described herein, when the known expanded geometry has changed, for example when a force is exerted by a tissue wall on assembly 130. System 10 can include one or more algorithms that use distance information data to localize, or allow an operator to localize, one or more devices of system 10. Alternatively or additionally, system 10 can include one or more algorithms that use distance information data to navigate, or allow an operator to navigate, one or more devices of system 10. The localization and/or navigation can comprise real-time or near real-time localization and/or navigation. The signals applied to any of the electrodes of system 10 can include constant or variable currents and/or voltages and/or other processed values.

Referring now to FIG. 3, a side view of a distal portion of the system of FIG. 1A is illustrated, where the diagnostic catheter has been retracted into the sheath. Diagnostic catheter 100 has been retracted into sheath 50 such that splines 131 and other components of expandable assembly 130 are in a collapsed or unexpanded state. Ablation catheter 200 has been slightly retracted into shaft 120 of diagnostic catheter 100 such that ablative element 261 remains partially exposed. Retraction of diagnostic catheter 100 and/or ablation catheter 200 can be performed by an operator grasping the relevant proximal portion (e.g. a handle) and moving the device proximally relative to sheath 50.

Shaft 120 of diagnostic catheter 100 can include braid 121. In some embodiments, braid 121 is positioned between an inner layer and an outer layer of shaft 120. Portions or all of braid 121 can include conductors, for example a helical or other arrangement of conductors integral to, positioned within and/or passing through braid 121 and operably connected to electrodes 141 and/or ultrasound transducers 151. In the illustrated embodiment, conductor 125 connects to wire 142 at connection point 143 (e.g. a solder connection point that operably connects to electrode 141). Similarly, conductor 124 connects to wire 152 at connection point 153 (e.g. a solder connection point that operably connects to ultrasound transducer 151). In some embodiments, conductors 124 and/or 125 include a standard wire with an insulation covering. Alternatively, conductors 124 and/or 125 include a coaxial cable, such as a coaxial cable with a diameter of approximately less than 0.012 inches. In some embodiments, conductors 124 and/or 125 are not part of braid 121, but rather pass through braid 121 and/or pass along an inner or outer surface of braid 121.

Also shown in FIG. 3 is the inclusion of pull wires and anchors for sheath 50, diagnostic catheter 100 and ablation catheter 200, each set configured to steer their respective device. Sheath 50 includes pull wire 52 and anchor 53 which can be connected to a lever, a cam, or other wire control mechanism which is operably connected to a knob or slide positioned on a handle, all not shown but located at a proximal end of sheath 50. Similarly, diagnostic catheter 100 includes pull wire 122 and anchor 123, and ablation catheter 200 includes pull wire 222 and anchor 223, each pull wire 122 and 222 typically controlled as described above by a control on a handle. Each device can be independently controlled via its respective steering pull wire and anchor, however if desired two or more devices can be controlled in concert, such as via a single control. Each device can comprise multiple pull wires, not shown but configured to provide multiple degrees of steering freedom.

Figure 4:
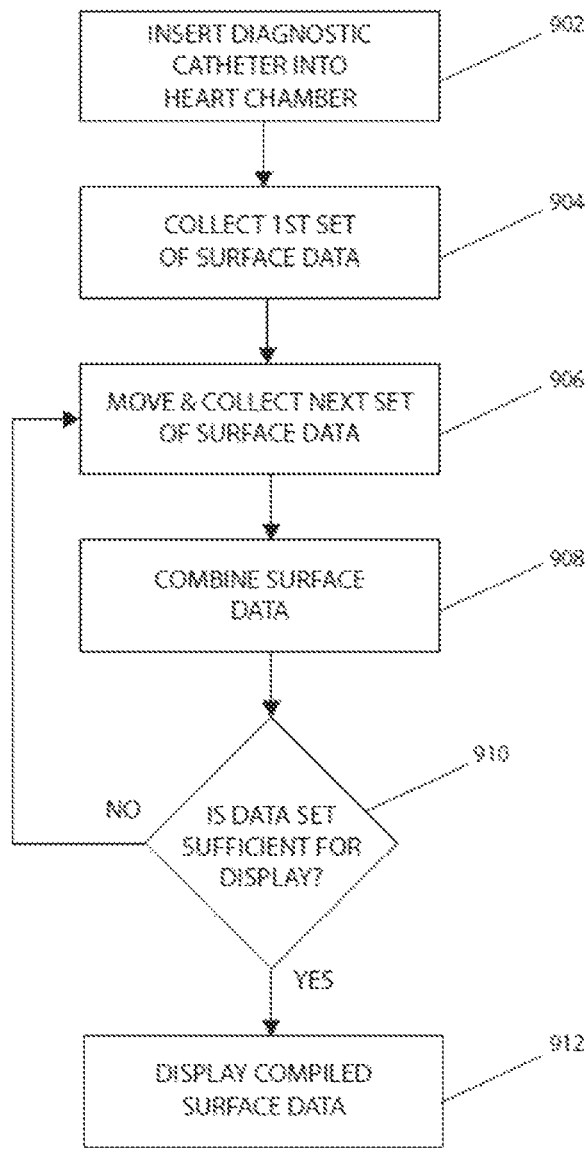
FIG. 4 is a flow chart of a method for mapping a 3-D space within a body using the system, according to aspects of the present invention.

Referring now to FIG. 4, a flow chart of a method for mapping a 3-D space within a body using the system of the present invention is illustrated. In STEP 902, a diagnostic catheter is inserted into a heart chamber, for example the left atrium, the right atrium, the left ventricle, or the right ventricle. The diagnostic catheter can be the same as or similar to diagnostic catheter 100 described herein. The diagnostic catheter can be inserted through previously inserted transseptal sheath, for example sheath 50 described herein. The diagnostic catheter includes one or more distance measurement elements, such as ultrasound transducers 151 described herein. A treatment device such as ablation catheter 200 can also be inserted into a heart chamber, either simultaneously with the diagnostic catheter (e.g. when the ablation catheter shaft resides within a lumen of the diagnostic catheter), or it can be inserted subsequent to the insertion of the diagnostic catheter, for example at a time after a 3-D map of the heart chamber has been created. The treatment device can be inserted through a lumen of the diagnostic catheter so that only a single transseptal puncture is required, as has been described in reference to FIG. 1A hereabove.

In STEP 904, a first set of surface data is collected via one or more ultrasound transducers positioned on the diagnostic catheter such as ultrasound transducers 151 described herein. Alternatively or additionally, surface data can be collected from ultrasound transducers positioned on a separate device such as device 200, 500, 600, 700 and/or an external device such as an external ultrasound device or other accessory device such as device 800 of FIG. 6. Data collected from the ultrasound transducers of device 100, 200, 500, 600, 700, and/or 800 can include distance information such as the distance from any ultrasound transducer to tissue such as cardiac tissue. Optionally, electrical information can also be collected via one or more electrodes positioned on a device, such as electrodes 141 described herein, or one or more electrodes positioned on one or more devices such as devices 100, 200, 500, 600 and/or 700 described herein. The electrical information can be used to determine distances between devices or device components, and it can be used to determine a geometric change in a device that occurs when a force is imparted, such as by using the algorithms described in reference to FIG. 2B hereabove. The electrical information can be collected simultaneously or synchronously with the data collected from the ultrasound transducers. In some embodiments, data is collected during multiple heart cycles where sequential sets of data can be correlated to a particular point in the heart cycle, for example data sets that are coordinated with a surface ECG recording that is simultaneously collected.

In STEP 906, the diagnostic catheter and/or any device including ultrasound transducers and/or electrodes is repositioned within the heart chamber so that a next set of surface data can be collected, similar to the collection of data in STEP 904.

In STEP 908, any or all sets of collected surface data are combined via a signal processing unit, for example signal processing unit 300 of FIG. 6. Multiple sets of ultrasound distances can be combined to generate a point cloud of surface points. When enough points are combined to satisfy a threshold for density and uniformity of distribution, a high-resolution reconstruction of the chamber surface can be "meshed" across the point cloud and displayed as an anatomical three-dimensional model. To reach this threshold, the relative position of the array is localized through time so that all subsequent acquired distances are translated back to a universal origin in the coordinate system and thereby combined into a single set of surface points. Once surface reconstruction is complete, the distances from the surface to any element and the voltage reading of that element can be used to calculate charge source values with respect to time. The charge source values; unipolar voltage or bipolar voltage values; monophasic action potential values; or other processed physiologic parameters; and combinations of these, can then be displayed upon the surface reconstruction.

In STEP 910, the signal processing unit can include an algorithm to determine or to assist in determining if the combined data is sufficient for display. This step can be a manual step, for example where a clinician can determine if the data is sufficient based on one or more outputs provided by the signal processing unit. Alternatively or additionally, this can be an automated step, for example where a threshold algorithm of the signal processing unit determines if the data points are within a particular range of values, or if the amount of collected data points meet a minimum number of sufficient data points. If the data points are determined to be insufficient, the method repeats beginning at STEP 906 where a next set of data is collected.

If the data is found to be sufficient in STEP 910, the method proceeds to STEP 912 where a 3-D map is displayed. The surface data collected from the ultrasound transducers or other transducers can be used to create an anatomical map of the heart chamber, and the surface data collected from the electrodes or other sensors can be used to create an electrical map of the heart chamber. The anatomical and electrical maps can be superimposed on one another. Using the electrical data, an algorithm can be employed to create a dipole density map. Details related to an applicable algorithm is disclosed in Applicant's co-pending international application, Serial Number PCT/US2012/028593, entitled Device and Method For the Geometric Determination of Electrical Dipole Densities on the Cardiac Wall, the entirety of which is incorporated herein. The anatomical and electrical maps can be overlaid to create a comprehensive 3-D map of the heart chamber. The data can represent a sequential set of data points corresponding to the beating cycle of the heart and associated heart wall motion (e.g. the repeated cycles of systole and diastole).

All data can be stored in memory by the signal processing unit or another component of the system of the present invention, such as for further processing, playback, or any other desired presentation or analysis.

Figure 5:
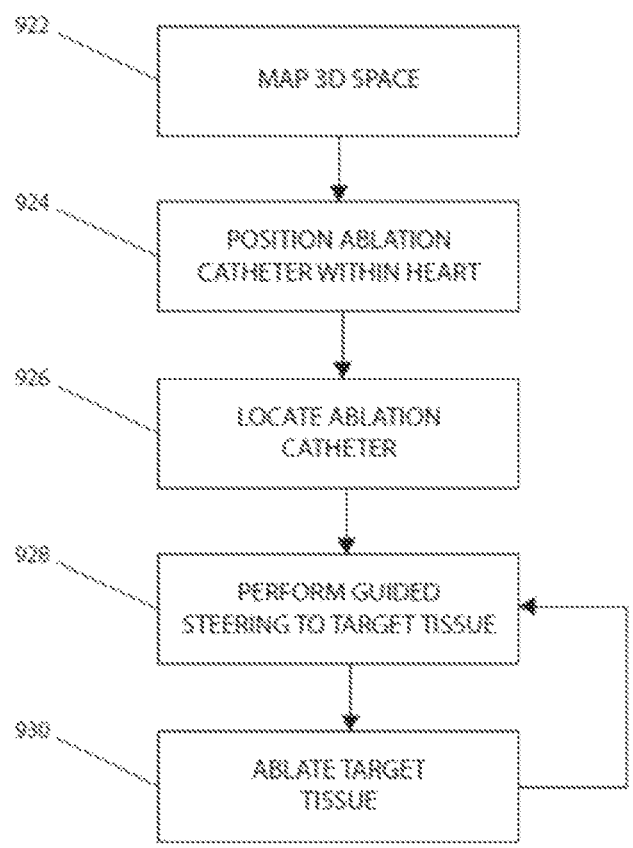
FIG. 5 is a flow chart of a method for localizing an ablation catheter within a body, using a 3-D mapping method such as that in FIG. 4, in accordance with aspects of the present invention.

Referring now to FIG. 5, a flow chart of a method for localizing an ablation catheter within a body using the system of the present invention is illustrated. In STEP 922, a 3-D electrical and/or anatomical map of a heart chamber is created, for example via the method disclosed in FIG. 4.

In STEP 924, an ablation catheter is positioned within the mapped heart chamber. The ablation catheter can be the same as or similar to ablation catheter 200 and/or 600 described herein. In one embodiment, the ablation catheter can be inserted in a lumen of a diagnostic catheter, for example diagnostic catheter 100 as has been described herein.

In STEP 926, the ablation catheter is located, such as a location in relation to the patient's anatomy and/or another device of the system of the present invention. An ablation catheter such as catheter 200 or 600 of FIG. 6 can be located using a triangulation technique, such as that described in reference to FIG. 2 hereabove. The triangulation technique can utilize recorded signals from multiple electrodes positioned in an expandable assembly, such as expandable assembly 130 described herein, and one or more energy delivery elements, such as electrodes 241 or 641 of catheters 200 or 600, respectively, of FIG. 6.

In STEP 928, the ablation catheter is steered to target tissue under guidance, such as while being navigated by the system of the present invention using the triangulation techniques described herein. Detail related to an applicable steering mechanism is described in detail in reference to FIG. 3 hereabove. In one embodiment, the triangulation technique of FIG. 2A is repeated continuously or semi-continuously, such as to provide a feedback loop used by an operator to steer the catheter. A feedback loop can include robotic or other automatic guidance of a catheter, for example a computer system, such as signal processing unit 300 of FIG. 6, can control steering, advancement and/or retraction of one or more catheters, such as via steering and linear motion assemblies in the handle of the catheter. In an alternate embodiment, visual feedback can be provided to an operator, such that the operator can perform manual steering, advancement and retraction of one or more catheters, while being provided catheter position information.

In STEP 930, the target tissue is ablated. The ablation catheter includes an ablation element that can include one or more electrodes; an energy delivery element configured to deliver cryogenic energy such as a cryogenic balloon; a laser delivery element such as a laser diode; an optical fiber configured to deliver ablative energy; a microwave energy delivery element; an ultrasound energy delivery element; a drug or other agent delivery element; and combinations of these. In the case where the ablation element includes one or more electrodes, the ablation element can include radiofrequency electrodes. In the case of multiple electrodes, the electrodes can be configured for bipolar and/or monopolar energy delivery. In some embodiments, the ablation element includes an array of elements such as in catheter 600 of FIG. 6. Further, the ablation catheter can be operably connected to an energy delivery unit, such as energy delivery unit 400 of FIG. 6.

STEPs 928 and 930 can be repeated one or more times, such as until the treatment is complete or otherwise ceased.

Referring now to FIG. 6, a schematic of an embodiment of a mapping and ablating system is illustrated. System 10 includes diagnostic catheter 100 and can also include sheath 50, ablation catheter 200, second diagnostic catheter 500, second ablation catheter 600, and/or accessory catheter device 700, each described in turn with reference to this figure. System 10 includes signal processing unit (SPU) 300, such as a computer system used to receive signals to produce electrical, anatomical and/or device mapping information. System 10 can include energy delivery unit (EDU) 400, such as an electrical or other energy delivery system that provides energy to one or more ablation elements of system 10, as are described herebelow. System 10 can include an accessory device 800, such as an imaging device comprising an externally applied ultrasound probe. System 10 can include one or more visual displays, such as one or more visual displays integral to SPU 300, EDU 400 or another device or component of system 10. The various components of system 10 can be electrically and/or mechanically connected by one or more cables, such as cables including electric wires and/or optical fibers to transmit data and/or power. In some embodiments, SPU 300, EDU 400 and/or robotic control assembly 850 transfer information to or from each other, such as via the wired or wireless communication pathways shown in FIG. 6.

Diagnostic catheter 100 includes expandable assembly 130 positioned at the distal end of shaft 120. Expandable assembly 130 can be resiliently biased in the radially expanded position shown in FIG. 6 or it can include a means of manual expansion, such as has been described hereabove. Expandable assembly 130 includes multiple splines 131, such as splines 131a and 131b shown. The distal ends of splines 131 can be configured in a ring-shaped geometry, opening 135, such as is described in reference to FIG. 1A hereabove. Expandable assembly 130 includes electrodes 141a and 141b and ultrasound transducers 151a and 151b, having the same or similar functionality as electrodes 141 and ultrasound transducers 151 described in FIG. 1A. Diagnostic catheter 100 typically includes four or more electrodes 141, such as an array of two to ten splines 131 where each spline 131 including four to ten electrodes 141. Diagnostic catheter 100 typically includes four or more ultrasound transducers 151, such as an array of two to ten splines 131 each spline 131 including four to ten ultrasound transducers 151. Diagnostic catheter 100 includes shaft 120 having a lumen configured to slidingly receive the shaft of a separate catheter, such as shaft 220 of ablation catheter 200. Handle 110, located at the proximal end of shaft 120, includes pigtail 113 where one or more shafts, simultaneously or sequentially, can be inserted to enter lumen 126 and to exit the distal end of shaft 120. Diagnostic catheter 100 can be inserted into a heart chamber, for example via a transseptal sheath, such as sheath 50. Handle 110 can include one or more controls, such as control 115. Control 115 can be constructed and arranged to allow an operator to perform an action selected from the group consisting of: steer shaft 120; radially expand assembly 130; radially contract assembly 130; and combinations of these. Control 115 can be operably connected to a mechanism within handle 110, mechanism not shown but typically a mechanism selected from the group consisting of: a control cable motion assembly such as a control cable motion assembly connected to a steering pull wire as described herein; a linear motion assembly constructed and arranged to advance and/or retract a control rod such as a control rod attached to assembly 130 to expand and/or retract assembly 130 as described herein; and combinations of these.

System 10 can include first ablation catheter 200 having a similar construction to ablation catheter 200 of FIG. 1A. Ablation catheter 200 includes handle 210 at the proximal end of shaft 220 and ablation element 261 at the distal end of shaft 220. Ablation element 261 can include an electrode that is configured to receive one or more forms of energy. Ablation catheter 200 can include one or more electrodes 241 and one or more ultrasound transducers 251, having the same or similar functionality as electrodes 141 and ultrasound transducers 151 described in reference to FIG. 1A hereabove, such as to provide anatomical, electrical and/or device mapping information to SPU 300 and/or another component of system 10. Handle 210 can include one or more controls such as control 215. Control 215 can be constructed and arranged to allow an operator to perform an action selected from the group consisting of: steer shaft 220; activate energy delivery by ablation element 261; adjust ablation delivery by ablation element 261; control an electrical connection to electrode 241 and/or ultrasound transducer 251; and combinations of these. Control 215 can be operably connected to a mechanism within handle 210, mechanism not shown but typically a mechanism selected from the group consisting of: a control cable motion assembly such as a control cable motion assembly connected to a steering pull wire as described herein; a linear motion assembly constructed and arranged to advance and/or retract a control rod; an electric switch; and combinations of these.

System 10 can include second diagnostic catheter 500 having handle 510 at the proximal end of shaft 520 and array 530 at the distal end of shaft 520. Array 530 can include recording electrodes 591 configured to record electrical activity. In one embodiment, array 530 can include electrodes 591 arranged in a spiral array so as to be placed in the coronary sinus or a pulmonary vein, such as to record electrical activity therein. Diagnostic catheter 500 can include one or more electrodes 541 and one or more ultrasound transducers 551, having the same or similar functionality as electrodes 141 and ultrasound transducers 151 described in reference to FIG. 1A hereabove, such as to provide anatomical, electrical and/or device mapping information to SPU 300 and/or another component of system 10. Handle 510 can include one or more controls such as control 515. Control 515 can be constructed and arranged to allow an operator to perform an action selected from the group consisting of: steer shaft 520; radially expand and/or contract array 530; control an electrical connection to electrodes 591, electrode 541 and/or ultrasound transducer 551; and combinations of these. Control 515 can be operably connected to a mechanism within handle 510, mechanism not shown but typically a mechanism selected from the group consisting of: a control cable motion assembly such as a control cable motion assembly connected to a steering pull wire as described herein; a linear motion assembly constructed and arranged to advance and/or retract a control rod; an electric switch; and combinations of these.

System 10 can include second ablation catheter 600 having handle 610 at the proximal end of shaft 620 and array 630 at the distal end of shaft 620. Array 630 can include electrodes 691 configured to record electrical activity. In one embodiment, array 630 can include electrodes 691 arranged in a linear or a two-dimensional array. Ablation catheter 600 can include one or more electrodes 641 and one or more ultrasound transducers 651, having the same or similar functionality as electrodes 141 and ultrasound transducers 151 described in reference to FIG. 1A hereabove, such as to provide anatomical, electrical and/or device mapping information to SPU 300 and/or another component of system 10.

Handle 610 can include one or more controls such as control 615. Control 615 can be constructed and arranged to allow an operator to perform an action selected from the group consisting of: steer shaft 620; radially expand and/or contract expandable assembly 630; activate energy delivery by electrodes 691; adjust energy delivery by electrodes 691; control an electrical connection to electrode 641 and/or ultrasound transducer 651; and combinations of these. Control 615 can be operably connected to a mechanism within handle 610, mechanism not shown but typically a mechanism selected from the group consisting of: a control cable motion assembly such as a control cable motion assembly connected to a steering pull wire as described herein; a linear motion assembly constructed and arranged to advance and/or retract a control rod; an electric switch; and combinations of these.

System 10 can include EDU 400 configured to deliver energy to any or all of the catheters and/or devices of system 10, for example catheters 100, 200, 500, 600, and 700 via wires 112, 212, 512, 612, and 712, respectively. Typical energy types include but are not limited to: radiofrequency energy; cryogenic energy; laser energy; light energy; microwave energy; ultrasound energy; chemical energy; and combinations of these. In one example, EDU 400 delivers energy to ablation element 261 of ablation catheter 200. EDU 400 can provide ablation energy to any ablation element of system 10, such as electrodes 691 of ablation catheter 600. System 10 can include grounding pad 420, shown attached to the back of the patient P, such that EDU 400 can deliver monopolar radiofrequency energy, such as via treatment elements 261, electrodes 691, or any electrode-based ablation element of system 10. EDU 400 can be configured to deliver bipolar and/or unipolar radiofrequency energy between any two electrodes in relative proximity to each other, such as two electrodes 691 of ablation catheter 600.

System 10 includes SPU 300 configured to send and/or record signals to and/or from any or all of the catheters and/or devices of system 10, for example catheters 100, 200, 500, 600, and 700 via wires 111, 211, 511, 611, and 711, respectively. In some embodiments, SPU 300 can send and/or record signals to and/or from accessory device 800 and/or body surface electrodes 820, such as when body surface electrodes 820 are positioned on the chest and abdomen of patient P as shown. For example, SPU 300 can record electric signals such as ultrasonic reflections from any or all of the ultrasound transducers of system 10 and can record current and/or voltage signals from any or all of the electrodes of system 10. The ultrasound transducers can be included on any or all of the catheters and/or other devices of system 10 (e.g. any of transducers 151a, 151b, 251, 551, 651, and 751). Similarly, the recording electrodes can be included on any or all of the catheters and/or other devices of system 10 (e.g. any of electrodes 141a, 141b, 241, 541, 641, and 741). Using the various recorded signals, SPU 300 can perform one or more algorithmic functions and other mathematical calculations on data extracted from the recorded signals. These calculations can result in output selected from the group consisting of: distance measurements; anatomical maps; device position maps; electrical maps; dipole maps; and combinations of these, such as are described in reference to FIG. 4 hereabove. Additionally, SPU 300 can provide catheter guidance or other device position information, such as is described in reference to FIG. 5 hereabove. In some embodiments, SPU 300 can include a electrical signal source such as a current source that can be coupled to electrodes 141a and 141b of diagnostic catheter 100, for example to collect data to create a dipole density map and/or to perform distance measurements as has been described in detail in reference to FIGS. 2A and 2B hereabove.

SPU 300 and/or other components of system 10 can be configured as a distance measurement assembly, such as to produce distance measurement data as is described in reference to FIGS. 2A and 2B hereabove. System 10 can be configured to produce distance measurement data between any two or more locations selected from the group consisting of: a location of a body inserted component or assembly of system 10 such as a location of a system 10 electrode such as an electrode 141, 241, 541, 641, 741 and/or a location of a system 10 ultrasound transducer such as an ultrasound transducer 151, 251, 551, 651 or 751; a location of a system 10 component that is external to the patient's body such as a surface electrode 820; a location of the patient's anatomy such as a location on the wall of the left atrium or the left ventricle; and combinations of these. In some embodiments, the distance between two splines 131 is determined by the distance measurement assembly of system 10. In some embodiments, the distance between a location on a first catheter and a location on a second catheter is determined by the distance measurement assembly of system 10, such as a location on diagnostic catheter 100 and a location on ablation catheter 200. In some embodiments, the distance measurement assembly of system 10 can utilize a determined and/or an approximated value for the impedance of blood and/or tissue, to perform one or more distance measurements. Impedance values used by system 10 in one or more algorithms can vary from patient to patient, and they can vary for one location to another location in a single patient. Impedance values can be determined, calibrated or otherwise improved by system 10, such as by performing a distance measurement between two system 10 components whose separation distance is fixed or otherwise known and determining an impedance value to be used in a subsequent calculation. Multiple impedance values, determined and/or approximated, can be averaged and the averaged value used in a subsequent calculation.

SPU 300 and/or EDU 400 typically include one or more output devices, such as output devices selected from the group consisting of: a visual display such as a touch-screen display; an audio device such as a speaker; a tactile devices such as operator worn vibrating bands; and combinations of these. In some embodiments, information such as electrical, anatomical and/or device mapping information can be provided to an operator of system 10 via a visual display integral to SPU 300. In some embodiments, information such as ablation energy delivery information can be provided to an operator of system 10 via a visual display integral to EDU 400.

System 10 can include an accessory device 800, for example an imaging device configured to produce an image of the patient's anatomy. Anatomical and other information can be provided by device 800 to SPU 300 via cable 804, such that SPU 300 can process the provided information in one or more algorithms such as to produce information for an operator, such as electrical, anatomical and/or device mapping information. In the embodiment of FIG. 6, accessory device 800 includes ultrasound generator 801 which is operably connected to an ultrasound probe 802 via cable 803. Anatomical images are produced when probe 802 is positioned proximate the patient's skin, such as in combination with an ultrasonic gel known to those of skill in the art. Generator 801 can include an output device, such as a visual display to provide a visual image of the patient's anatomy recorded by device 800. In some embodiments, the visual display is integral to SPU 300 and/or EDU 400.

In some embodiments, generator 801 can communicate with (e.g. send and receive signals to and from) one or more other ultrasound transducers, such as one or more of ultrasound transducers 151*a*, 151*b*, 251, 551, 651 and/or 751.

Alternatively or additionally, accessory device 800 can comprise a recording device selected from the group consisting of: transesophageal echocardiography device; intracardiac echocardiography device; lasso diagnostic catheter recording device; coronary sinus diagnostic catheter recording device; and combinations of these.

System 10 can include catheter device 700, typically configured to be slidingly received by shaft 120 of diagnostic catheter 100. Catheter device 700 includes handle 710 which is fixedly attached to a flexible shaft 720. Shaft 720 includes distal end 729. Catheter device 700 can include one or more electrodes 741 and one or more ultrasound transducers 751, having the same or similar functionality as electrodes 141 and ultrasound transducers 151 described in reference to FIG. 1A hereabove, such as to provide anatomical, electrical and/or device mapping information to SPU 300 and/or another component of system 10. Electrodes 741 and/or ultrasound transducers 751 can be mounted to shaft 720 and/or to an expandable assembly, not shown but as has been described hereabove. Handle 710 can include one or more controls such as control 715. Control 715 can be constructed and arranged to allow an operator to perform an action selected from the group consisting of: steer shaft 720; control an electrical connection to electrode 741 and/or ultrasound transducer 751; and combinations of these. Control 715 can be operably connected to a mechanism within handle 710, mechanism not shown but typically a mechanism selected from the group consisting of: a control cable motion assembly such as a control cable motion assembly connected to a steering pull wire as described herein; a linear motion assembly constructed and arranged to advance and/or retract a control rod; an electric switch; and combinations of these. In some embodiments, catheter device 700 comprises a catheter selected from the group consisting of: a catheter with helical array of electrodes such as a lasso catheter; a pacing catheter; an energy delivery catheter such as a catheter constructed and arranged to deliver radiofrequency energy, microwave energy, cryogenic energy, laser energy and/or ultrasound energy; a drug or other agent delivery catheter such as a catheter constructed and arranged to deliver antiarrhythmic medications, stem cells, or other biologic agents; a mechanical device delivery catheter such as a catheter constructed and arranged to deploy (e.g. out of distal end 729 of shaft 720) a robotic navigation or manipulation device, an atrial appendage closure device, a valve replacement device, a tissue biopsy device, or other diagnostic or therapeutic device delivered through a lumen of shaft 710; and combinations of these.

System 10 can include robotic control assembly 850, such as a robot or other assembly configured to control one or more linkages, cables or other robotic control mechanisms. Robotic control assembly 850 includes control conduit 859 which can be operably attached to one or more robotically manipulatable assemblies of system 10. As shown in FIG. 6, control conduit can be operably attached to one or more of: diagnostic catheter 100 via cable 851 ablation catheter 200 via cable 852; second diagnostic catheter 500 via cable 853; second ablation catheter 600 via cable 854; and catheter device 700 via cable 855. Each catheter device of system 10 can include one or more robotically manipulatable assemblies such as a steering mechanism and/or a catheter shaft advancing and/or retracting mechanism. In some embodiments, robotic control assembly 850 is used to steer, advance and/or retract diagnostic catheter 100 and/or ablation catheter 200. Robotic control assembly 850 can be used to manually (e.g. operator driven), semi-automatically (e.g. operator driven and system 10 driven) or automatically (e.g. fully driven by system 10) navigate one or more catheter devices of system 10. System 10 can be configured to receive operator (e.g. clinician) input information, such as clinician input information used to semi-automatically or automatically navigate one or more catheter devices of system 10.

Robotic control assembly 850 can navigate one or more devices or assemblies based on an analysis of one or more of: dipole mapping information recorded by at least one dipole mapping electrode and distance information recorded by at least one ultrasound transducer. Robotic control assembly 850 can navigate one or more devices or assemblies based on a distance measurement performed between a first electrode and second electrode of system 10, such as has been described in reference to FIGS. 2A an 2B hereabove.

In some embodiments, manual or automatic navigation can be based upon or otherwise include an assessment of contact of a portion of system 10 with tissue. Contact of a portion of system 10 with tissue can be determined by analyzing distance signals received by one or more ultrasound transducers of system 10, such as ultrasound transducers 151*a*, 151*b*, 251, 551, 651 and/or 751. Determination of sufficient contact may be compared to a threshold (e.g. a distance or pressure threshold), such as a threshold that is adjustable by a clinician operator of system 10 (e.g. a threshold included in clinician input information).

Figure 7A:
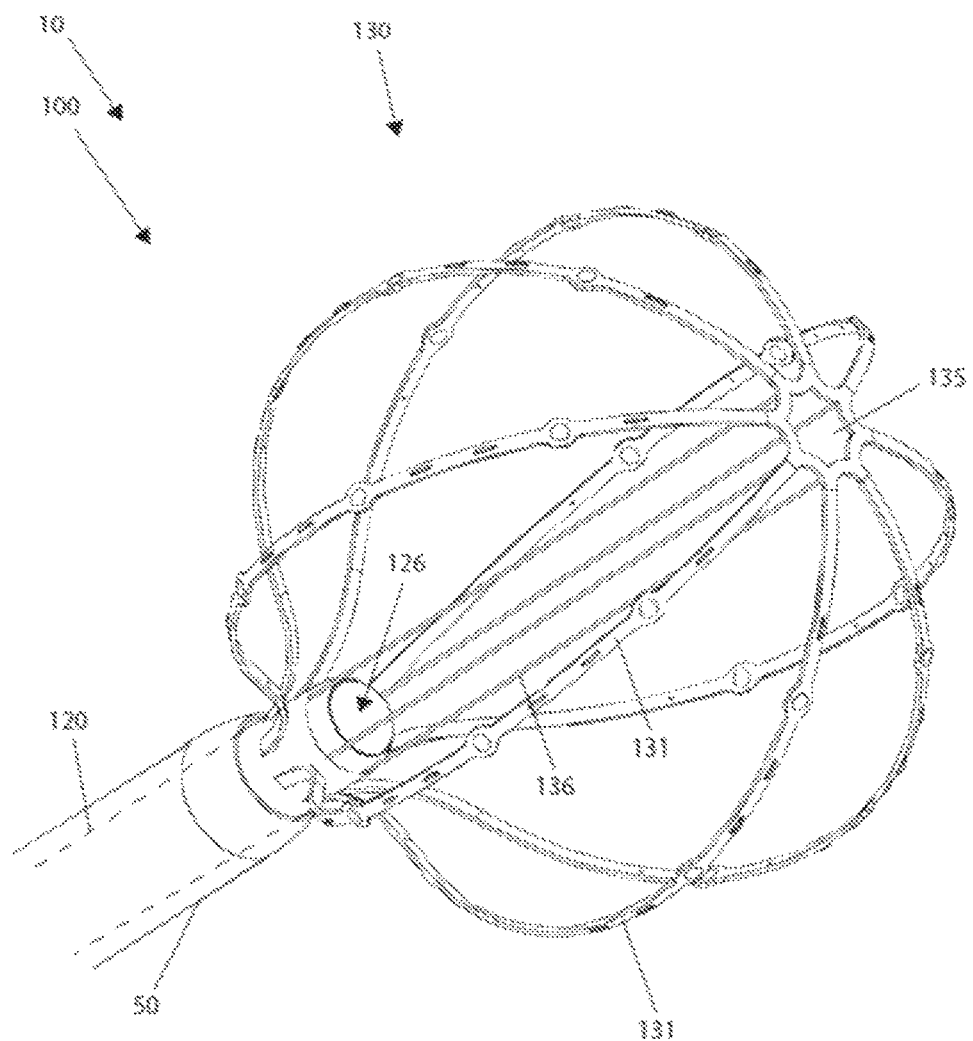
FIG. 7A is a perspective view of a diagnostic catheter, including guide elements, in accordance with aspects of the present invention.

Referring now to FIG. 7A, a perspective view of a distal portion of a diagnostic catheter is illustrated, including guide elements for directing a catheter. Diagnostic catheter 100 of FIG. 7A includes shaft 120, lumen 126, expandable assembly 130 including splines 131, and opening 135, each typically of similar construction and arrangement as is described to the similar components of catheter 100 of FIG. 1A. Diagnostic catheter 100 is typically part of system 10, including sheath 50 through which shaft 120 has been inserted. Diagnostic catheter 100 further includes guide elements 136. Guide elements 136 can comprise two or more flexible or rigid filaments (e.g. nickel titanium alloy filaments) configured to provide a biasing force upon a shaft of a second catheter inserted within shaft 120 of catheter 100. The biasing force can be configured cause a distal portion of shaft 120 to tend to remain relatively straight and geometrically centered within expandable assembly 130. The biasing force can be used to direct ablation element 261 and the distal portion of shaft 220 to pass through opening 135, as shown in FIG. 1A. Once advanced distal to opening 135, ablation element 261 can positioned to contact and/or deliver energy to tissue such as heart wall tissue.

Figure 7B:
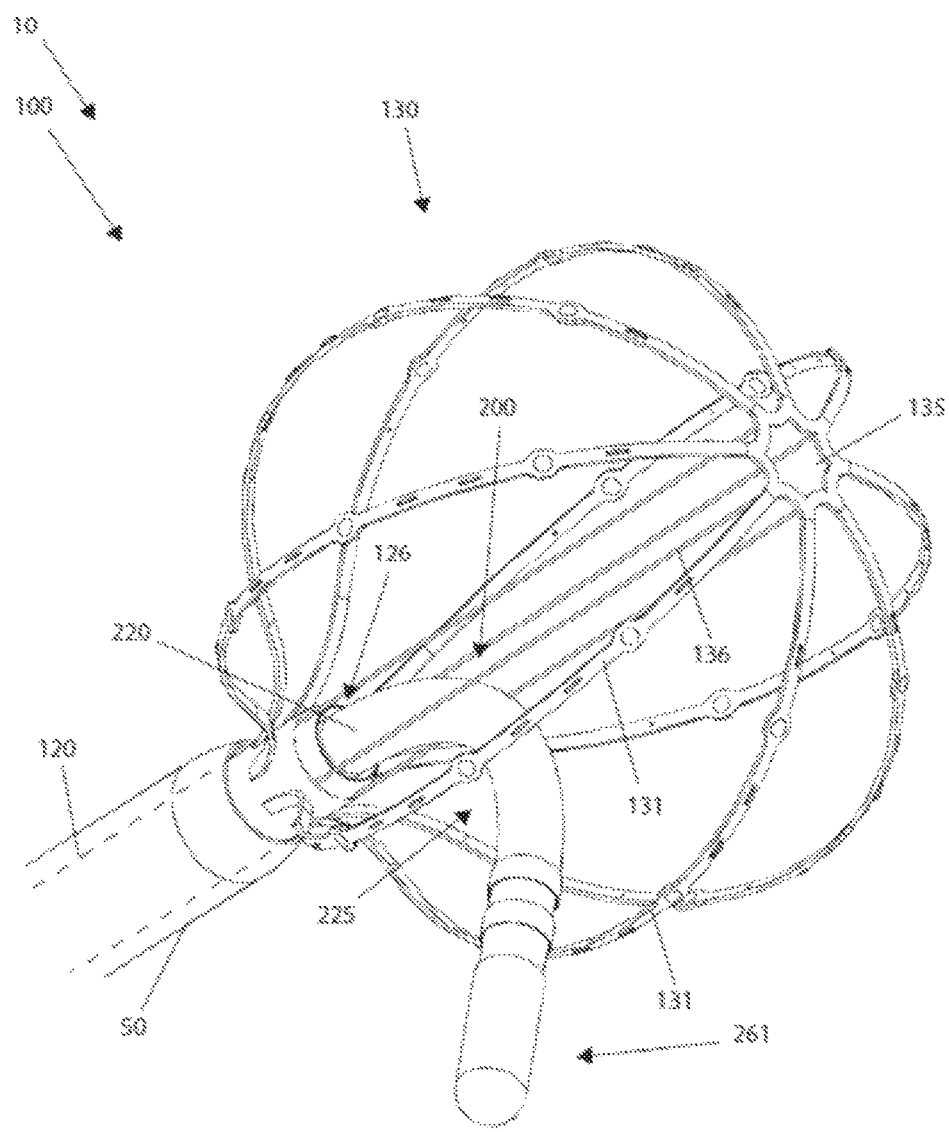
FIG. 7B is a perspective view of the diagnostic catheter of FIG. 7A, including an ablation catheter that is steered outside of the guide elements, in accordance with aspects of the present invention.

In some embodiments, guide elements 136 are constructed and arranged to allow the distal end of an inserted catheter to be steered to pass between two guide elements 136 (e.g. by overcoming any biasing force applied by guide elements 136), and avoid passing through opening 135. Referring now to FIG. 7B, the distal portion 225 of shaft 220 of ablation catheter 200 has been steered to pass between two guide elements 136. Shaft 220 has been further advanced and/or steered to also pass between two splines 131 as shown, without passing through opening 135. Once advanced radially out from splines 131, ablation element 261 can be positioned to contact and/or deliver energy to tissue such as heart wall tissue. Numerous forms of guiding elements can be included to allow both a biased linear advancement of an inserted shaft as well as a curvilinear exit pathway between two guiding elements 136 and two splines 131. Guide elements 136 can be spaced or otherwise constructed and arranged such as to allow or prevent the distal portion of ablation catheter 200 to exit the expandable assembly 130 prior to passing through opening 135.

In some embodiments, guide elements 136 are each fixed on their proximal and distal ends to expandable assembly 130 as shown. In these embodiments, guide elements 136 can comprise an elastic material allowing each to stretch, such as to accommodate the expansion and contraction of assembly 130. Additionally, the elasticity of one or more guide elements 136 can be configured to bias expandable assembly 130 in a radially expanded state. Alternatively, guide elements 136 can be rigid, such as when their proximal ends are slidingly received by shaft 120, such as via one or more lumens 126 or finite length channels, not shown but of sufficient diameter and length to allow guide elements 136 to slide therein as expandable assembly 130 expands and collapses (i.e. un-expands or compacts). In alternative embodiments, guide elements 136 comprise a single tube construction, not shown but a hollow tube configured to guide a catheter or other elongate device to exit shaft 120 of diagnostic catheter 100 and pass through opening 135.

While the foregoing has described what are considered to be the best mode and/or other preferred embodiments, it is understood that various modifications can be made therein and that the invention or inventions can be implemented in various forms and embodiments, and that they can be applied in numerous applications, only some of which have been described herein. It is intended by the following claims to claim that which is literally described and all equivalents thereto, including all modifications and variations that fall within the scope of each claim.

What is claimed is:

1. An ablation system, comprising:
    an ablation catheter comprising:
        an elongate shaft with a distal portion; and
        at least one ablation element positioned on the ablation catheter shaft distal portion and configured to deliver energy to tissue;
    a diagnostic catheter comprising:
        an elongate shaft comprising a distal end, wherein the diagnostic catheter shaft is configured to slidingly receive the distal portion of the ablation catheter shaft;
        an expandable assembly mounted to the diagnostic catheter shaft and configured to transition from a compacted state to an expanded state;
        a plurality of dipole mapping electrodes coupled to the expandable assembly and configured to provide dipole density information;
        a plurality of ultrasound transducers coupled to the expandable assembly;
    a distance measurement assembly configured to drive the plurality of ultrasound transducers to produce anatomical geometry data, including data representing a distance between each ultrasound transducer of the plurality of ultrasound transducers and a tissue surface orthogonal to each ultrasound transducer in view of a shape of the expandable assembly; and
    a processing unit configured to employ the anatomical geometry data to create a three-dimensional map of an anatomical cavity into which it is placed and to produce a dipole density map from the dipole density information, wherein the processing unit is configured to drive a display to display the dipole density map in conjunction with the three-dimensional map of the anatomical cavity.

2. The system of claim 1, wherein the diagnostic catheter is further configured to provide information selected from the group consisting of:
    surface unipolar voltage information;
    surface bipolar voltage information;
    surface charge density information;
    monophasic action potential information; and
    combinations thereof.

3. The system of claim 1, further comprising a sheath with a distal end and wherein the expandable assembly is configured to radially expand as it exits the sheath distal end.

4. The system of claim 1, wherein the expandable assembly comprises a plurality of expandable members comprising at least one of a shape memory alloy, a shape memory polymer, or both.

5. The system of claim 1, wherein the expandable assembly comprises a plurality of bendable splines, each spline comprising a proximal end and a distal end, and a set of spaced dipole mapping electrodes.

6. The system of claim 5, wherein the set of spaced dipole mapping electrodes comprises at least 4 dipole mapping electrodes.

7. The system of claim 5, wherein each spline further comprises a set of spaced ultrasound transducers.

8. The system of claim 7, wherein the set of spaced ultrasound transducers comprises at least 4 ultrasound transducers.

9. The system of claim 5, wherein each spline further comprises at least two of the plurality of dipole mapping electrodes and at least two of the plurality of ultrasound transducers, and wherein on each spline, one or more of the plurality dipole mapping electrodes are disposed between two adjacent ultrasound transducers.

10. The system of claim 5, wherein each spline proximal end is fixedly attached at a location proximate the diagnostic catheter elongate shaft distal end, and each spline distal end is connected in a circumferential arrangement.

11. The system of claim 10, wherein the circumferential arrangement defines an opening when the expandable assembly is in an expanded state.

12. The system of claim 11, wherein the diagnostic catheter shaft comprises a distal portion defining a central axis, and wherein the opening is relatively centered about the axis and large enough to receive a distal end of the ablation catheter.

13. The system of claim 11, wherein the expandable assembly further comprising two or more guide elements configured to guide a distal end of the ablation catheter distal through the opening.

14. The system of claim 5, wherein the ablation catheter comprises a distal end, wherein each spline further comprises a mid-portion positioned between its proximal end and its distal end, and wherein the ablation catheter distal end is configured to be radially deflected to cause the ablation catheter distal end to pass between a first spline mid portion and a second spline mid portion when the bendable splines are in an expanded state.

15. The system of claim 1, wherein the plurality of dipole mapping electrodes comprise at least one dipole mapping electrode with an impedance of less than 10,000 ohms for frequencies above 0.1 hertz.

16. The system of claim 1, wherein the plurality of ultrasound transducer comprises an assembly selected from the group consisting of:

single or multi-element piezoelectric ceramics;
piezoelectric micro-machined ultrasound transducers (pMUT);
capacitive micro-machined ultrasound transducers (cMUT);
piezoelectric polymers; and
combinations thereof.

17. The system of claim 1, wherein each of the plurality of ultrasound transducers is disposed between two dipole mapping electrodes.

18. The system of claim 1, wherein the diagnostic catheter shaft comprises a wall comprising two or more electrical conductors positioned therein.

19. The system of claim 18, wherein the two or more electrical conductors comprise two or more coaxial cables.

20. The system of claim 1, wherein the ablation catheter comprises multiple electrodes configured to deliver energy and record electrical signals.

21. The system of claim 1, wherein the at least one ablation element comprises an ablation element selected from the group consisting of:
   an electrode;
   a vessel configured to deliver cryogenic energy;
   a laser diode;
   an optical fiber configured to deliver ablative energy;
   a microwave energy delivery element;
   an ultrasound energy delivery element;
   a drug or other agent delivery element; and
   combinations thereof.

22. The system of claim 1, wherein the distance measurement assembly is configured to deliver a signal to the diagnostic catheter plurality of ultrasound transducers, record a first generated signal from the diagnostic catheter plurality of ultrasound transducers, and produce a first set of distance information based on the recording of the first generated signal.

23. The system of claim 1, wherein the system comprises at least a first electrode and a second electrode and wherein the distance measurement assembly produces data representing the distance between the first electrode and the second electrode.

24. The system of claim 23, wherein the first electrode is configured to deliver an electrical signal, and the second electrode is configured to record the electrical signal delivered by the first electrode, and wherein the distance measurement assembly produces the data based on the recorded electrical signal.

25. The system of claim 23, wherein the first electrode comprises a dipole mapping electrode and wherein the ablation catheter comprises the second electrode and wherein the distance measurement assembly produces data representing a distance between the diagnostic catheter and the ablation catheter.

26. The system of claim 1, wherein the diagnostic catheter comprises at least two electrodes, and wherein the distance measurement assembly is configured to deliver a signal to the diagnostic catheter at least two electrodes, record a first generated signal from the diagnostic catheter at least two electrodes, and produce a first set of distance information based on the recording of the first generated signal, and wherein the first set of distance information represents a geometric configuration of the expandable assembly.

27. The system of claim 26, further comprising at least one body surface electrode, wherein the distance measurement assembly is further configured to deliver a signal to the at least one body surface electrode, record a second generated signal from the at least one body surface electrode, and produce a second set of distance information based on the recording of the second generated signal.

28. The system of claim 1, further comprising an energy source configured to provide energy to the at least one ablation element of the ablation catheter, wherein the energy source is configured to provide an energy form selected from the group consisting of:
   radiofrequency energy;
   cryogenic energy;
   laser energy;
   light energy;
   microwave energy;
   ultrasound energy;
   chemical energy; and
   combinations thereof.

29. The system of claim 1, further comprising an electrogram recording catheter.

30. The system of claim 1, further comprising a second ablation catheter, wherein the second ablation catheter is configured to be sliding received by the diagnostic catheter shaft.

31. The system of claim 1, further comprising a third catheter device configured to be slidingly received by the diagnostic catheter shaft, wherein the third catheter device comprises a device selected from the group consisting of:
   a catheter with helical array of electrodes;
   a pacing catheter; and
   an energy delivery catheter constructed and arranged to deliver radiofrequency energy, microwave energy, cryogenic energy, laser energy and/or ultrasound energy;
   a drug or other agent delivery catheter constructed and arranged to deliver antiarrhythmic medications, stem cells, or other biologic agents;
   a mechanical device delivery catheter; and
   combinations thereof.

32. The system of claim 1, wherein the three-dimensional map comprises an anatomical map of the cavity.

33. The system of claim 1, wherein the three-dimensional map comprises an electrical map of the cavity.

34. The system of claim 1 wherein the anatomical geometry information includes at least one of heart wall position information or heart wall thickness information.

* * * * *